(12) United States Patent
Mäkelä et al.

(10) Patent No.: US 11,680,092 B2
(45) Date of Patent: Jun. 20, 2023

(54) CIP2A VARIANT AND USES THEREOF

(71) Applicant: Turun yliopisto, Turun yliopisto (FI)

(72) Inventors: Eleonora Mäkelä, Turku (FI); Jukka Westermarck, Turku (FI)

(73) Assignee: TURUN YLIOPISTO, Turun Yliopisto (FI)

( * ) Notice: Subject to any disclaimer, the term of this patent is extended or adjusted under 35 U.S.C. 154(b) by 275 days.

(21) Appl. No.: 16/765,084

(22) PCT Filed: Nov. 20, 2018

(86) PCT No.: PCT/FI2018/050844
§ 371 (c)(1),
(2) Date: May 18, 2020

(87) PCT Pub. No.: WO2019/097122
PCT Pub. Date: May 23, 2019

(65) Prior Publication Data
US 2020/0354434 A1 Nov. 12, 2020

(30) Foreign Application Priority Data
Nov. 20, 2017 (FI) .................. 20176032

(51) Int. Cl.
| | | |
|---|---|---|
| *G01N 33/00* | (2006.01) | |
| *C07K 14/82* | (2006.01) | |
| *C07K 16/18* | (2006.01) | |
| *C07K 16/30* | (2006.01) | |
| *C12Q 1/6886* | (2018.01) | |
| *G01N 33/574* | (2006.01) | |

(52) U.S. Cl.
CPC .............. *C07K 14/82* (2013.01); *C07K 16/18* (2013.01); *C07K 16/30* (2013.01); *C12Q 1/6886* (2013.01); *G01N 33/57496* (2013.01); *C07K 2317/34* (2013.01); *C12Q 2600/118* (2013.01); *C12Q 2600/156* (2013.01)

(58) Field of Classification Search
CPC ........ C07K 14/82; C07K 16/18; C07K 16/30; C07K 2317/34; C12Q 1/6886; C12Q 2600/118; C12Q 2600/156; G01N 33/57496
See application file for complete search history.

(56) References Cited

U.S. PATENT DOCUMENTS

| | | | | |
|---|---|---|---|---|
| 6,919,193 B2 * | 7/2005 | Tang | ............ | C07K 14/47 424/94.6 |
| 2007/0083334 A1 * | 4/2007 | Mintz | ............ | G16B 40/00 702/19 |
| 2012/0070837 A1 | 3/2012 | Huang et al. | | |
| 2013/0115599 A1 | 5/2013 | Huang et al. | | |

FOREIGN PATENT DOCUMENTS

| | | |
|---|---|---|
| EP | 2 021 499 | 2/2009 |
| JP | 2009-519710 | 5/2009 |
| WO | 2007/078599 | 7/2007 |
| WO | 2007/104835 | 9/2007 |
| WO | WO2008051260 | * 5/2008 |

OTHER PUBLICATIONS

Office Action dated Jul. 2, 2021 in corresponding Japanese Application No. 2020-527797 (with translation), 10 pages.
Hyun Min Jung et al., "Tumor Suppressor miR-375 Regulates MYC Expression via Repression of CIP2A Coding Sequence Through Multiple miRNA-mRNA Interactions," Molecular Biology of the Cell, Jun. 1, 2013, vol. 24, pp. 1638-1648.
Christophe Come et al., "CIP2A is Associated with Human Breast Cancer Aggressivity," Clinical Cancer Research, vol. 15-16, Aug. 15, 2009, pp. 5092-5100.
Maria Ciccone, et al., "From the biology of PP2A to the PADs for therapy of hematologic malignancies", Frontiers in Oncology, published Feb. 16, 2015, vol. 5, Article 21, 10 pages.
Ion Cristóbal, et al., "SETBP1 overexpression is a novel leukemogenic mechanism that predicts adverse outcome in elderly patients with acute myeloid leukemia", Myeloid Neoplasia, Jan. 21, 2010, vol. 115, No. 3, 12 pages.
Melissa R. Junttila, et al., "CIP2A Inhibits PP2A in Human Malignancies", Cell, Jul. 13, 2007, vol. 130, pp. 51-62.
Anchit Khanna, et al., "Clinical significance of cancerous inhibitor of protein phosphatase 2A in human cancers", International Journal of Cancer, 2016, vol. 138, pp. 525-532.
Yuchun Li, et al., "HapMap-based study of CIP2A gene polymorphisms and HCC susceptibility", Oncology Letters, accepted May 15, 2012, vol. 4, pp. 358-364.
Elizabeth McDonald, "Cancerous Inhibitor of Protein Phosphate 2A (CIP2A) in Chronic Myeloid Leukemia", University of Liverpool, Oct. 2015, 264 pages.
Sami Ventelä, et al., "CIP2A is an Oct4 target gene involved in head and neck squamous cell cancer oncogenicity and radioresistance", Oncotarget, published Dec. 5, 2014, vol. 6, No. 1, pp. 144-158.
Sami Ventelä, et al., "CIP2A Promotes Proliferation of Spermatogonial Progenitor Cells and Spermatogenesis in Mice", PLoS One, Mar. 2012, vol. 7, Issue 3, 10 pages.
Search Report for FI Patent Application No. 20176032 dated May 9, 2018, 2 pages.

(Continued)

*Primary Examiner* — Lei Yao
(74) *Attorney, Agent, or Firm* — Nixon & Vanderhye, P.C.

(57) ABSTRACT

The present invention relates to a novel cancer-associated biomarker and different applications and uses thereof. More specifically, the invention relates to a novel splice variant of CIP2A denoted as NOCIVA, as well as binding bodies such as probes, amplification primers, and antibodies specific for the same. Also provided are various methods for detecting and prognosing cancer on the basis of said splice variant, and a kit for use in said methods.

1 Claim, 19 Drawing Sheets
Specification includes a Sequence Listing.

(56) References Cited

OTHER PUBLICATIONS

International Preliminary Report on Patentability for PCT/FI2018/050844 dated Oct. 21, 2019, 12 pages.
International Search Report for PCT/FI2018/050844 dated Jan. 25, 2019, 6 pages.
Written Opinion of the ISA for PCT/FI2018/050844 dated Jan. 25, 2019, 5 pages.
Terhune et al., "Early Polyadenylation Signals of Human Papillomavirus Type 31 Negatively Regulate Capsid Gene Expression", Journal of Virology, Sep. 2001, vol. 75, No. 17, pp. 8147-8157.

* cited by examiner

```
             V  S  E  Y  K  I  L  Q  D  D  P  R  L  I  T  P  L  A  F  A  L  T  S  D  N  R  E  Q
1492    GTAAGCTTCTACAAAATACTTCAGGACCCAGTTGATTACTCCTTTGCTTTAAGTCAGATAATAGAGAACA    1572
             V  Q  S  G  L  R  L  I  L  L  E  A  A  P  L  P  D  F  P  A  L  V  N  N  K  N  T
1573    AGTACAGTCTGGACTGAGAATATTATTGGAAGCTGCTCCACTGCCAGATTTCCTGCTTTAGTCAACAACAAAATACAC    1652
             Q  E  A  F  Q  V  T  S  *
1653    AGGAAGCTTTTCAAGTTACAAGTTAAAAAGTGGTCTCTGTAAAGCTCTTGCTCTGCATAAACTGGTA    1732
1733    ATCTGAACAGTGAAACATGAAACAAACTTCAAAGAGCTTCAAAGAGGAATCTGAGCCTCACTGAACATGGAAGCTTATCCCTTTCCCT    1812
1813    CTGTGTGTGAGGCCTTCCCACCATTTGACTGTGTCTTGGCCATTCCCGTCTTATTTGTGTAATAATTTTCTCTTT    1892
1893    GGGCATTATCTCAGAGTCCCATTTTATGCTTACTATTTAATGCCCTTATTTGACATTATCTTGGGCGGTTAATAAATGA    1972
1973    ATGTATAATTATGAAAAAAAAAAAAAAAAAAAAAAAAAAAA    2010
```

| Function of the protein | Gene | Overexpression in sample collection | FC > 2 |
|---|---|---|---|
| Known AML marker | WT1 | 84 % | 81 % |
| Known AML marker | EVI1 | 12 % | 10 % |
| Known AML marker / PP2A inhibitor | SET | 33 % | 10 % |
| PP2A inhibitor | CIP2A | 7 % | 2 % |
| CIP2A variant | NOCIVA | 78 % | 68 % |

Figure 3B

| Summary of the Number of Censored and Uncensored Values | | | | |
|---|---|---|---|---|
| Riskgroup | Total | Dead | Alive | Percent Alive |
| 1 | 21 | 4 | 17 | 80,95 |
| 2 | 37 | 18 | 19 | 51,35 |
| 3 | 22 | 16 | 6 | 27,27 |
| Tot. | 80 | 38 | 42 | 52,5 |

1 favourable [t(8;21), inv16, NMP1+, FLT3-ITD-]

2 intermediate [normal karyotype]

3 adverse [inv(3), t(v;11), 5q, -5, -7, abnl(17p), t(9;22), complex karyotype, monosomal karyotype

Figure 4A

| Variable | Wald Chi-Square | Pr > ChiSq |
|---|---|---|
| DgAge | 15,0763 | 0,0001 |
| Riskgroup | 14,7489 | 0,0006 |

Analysis of Maximum Likelihood Estimates

| Parameter | | Parameter Estimate | Standard Error | Chi-Square | Pr > ChiSq | Hazard Ratio | Label |
|---|---|---|---|---|---|---|---|
| DgAge | | 0,07654 | 0,01971 | 15,0763 | 0,0001 | 1,08 | Age at diagnosis |
| Riskgroup | 2 | 1,04723 | 0,55439 | 3,5682 | 0,0589 | 2,85 | Cytogenetic and molecular genetic risk group 2 |
| Riskgroup | 3 | 1,99647 | 0,56894 | 12,314 | 0,0004 | 7,363 | Cytogenetic and molecular genetic risk group 3 |

Figure 4B

| Variable | Difference between groups 1-2-3 | 1 vs 2 | 1 vs 3 | 2 vs 3 |
|---|---|---|---|---|
| CIP2Ae13 | - | - | - | - |
| CIP2Ae20 | - | - | - | - |
| NOCIVA | - | - | - | +/- (0.0743) |
| EVI | + (0.0050) | - | - | - |
| WT1 | +/- (0.0771) | - | - | - |
| SET | - | - | - | + (0.0530) |

Figure 4C

| Analysis of Maximum Likelihood Estimates OS ||||||
|---|---|---|---|---|---|
| Parameter | Parameter Estimate | Standard Error | Chi-Square | Pr > ChiSq | Hazard Ratio |
| DgAge | 0,06812 | 0,02123 | 10,2973 | 0,0013 | 1,07 |
| CIP2A e13 | -1,75284 | 0,99276 | 3,1174 | 0,0775 | 0,173 |
| NOCIVA | 0,41302 | 0,17827 | 5,3676 | 0,0205 | 1,511 |
| EVI1 | 0,23488 | 0,06649 | 12,4812 | 0,0004 | 1,265 |

Figure 4D

| Analysis of Maximum Likelihood Estimates OS | | | | |
|---|---|---|---|---|
| Parameter | Parameter Estimate | Standard Error | Chi-Square | Pr > ChiSq | Hazard Ratio |
| DgAge | 0,06178 | 0,02028 | 9,2817 | 0,0023 | 1,064 |
| EVI1 | 0,18819 | 0,06097 | 9,5281 | 0,002 | 1,207 |
| NOCIVA / CIP2A e13 | 0,00202 | 0,0007245 | 7,7594 | 0,0053 | 1,002 |

Figure 4F

CIP2A VARIANT AND USES THEREOF

This application is the U.S. national phase of International Application No. PCT/FI2018/050844 filed Nov. 20, 2018 which designated the U.S. and claims priority to FI Patent Application No. 20176032 filed Nov. 20, 2017, the entire contents of each of which are hereby incorporated by reference.

SEQUENCE LISTING

The instant application contains a Sequence Listing which has been filed electronically in ASCII format.

FIELD OF THE INVENTION

The present invention relates to a novel cancer-associated biomarker and different applications thereof. More specifically, the invention relates to a novel splice variant of CIP2A denoted as NOCIVA, as well as binding bodies such as probes, amplification primers, and antibodies specific for the same. Also provided are various methods for detecting and prognosing cancer on the basis of said splice variant, and a kit for use in said methods. Without being limited thereto, the invention concerns in particular lymphoid cancers such as acute myeloid leukaemia (AML).

BACKGROUND OF THE INVENTION

Acute myeloid leukemia (AML) is the most common acute leukemia affecting adults. Incidence of AML is 2 to 3 new cases per 100 000 inhabitants per year. AML is a heterogeneous clonal hematological malignancy that disrupts normal hematopoiesis and it is one of the most aggressively progressive cancer types. First curative therapies for AML were developed in the 1970s-80s and before this patients with AML had a dismal prognosis of only three months. In the 2010s 50% of the patients with AML under age 60-65 can obtain a full remission.

Advances in understanding the genetic diversity of AML have enabled identification of prognostic subgroups within AML cases. Classification of AML subtypes is also clinically relevant in order to optimize treatment strategies and to reduce treatment related mortality and relapse risk. Patients in good prognosis risk category are treated with chemotherapy, which allows up to 70% of the patients to go to full remission. Alternatively, treatment for those intermediate and poor prognosis patients for which it is suitable, is allogeneic stem cell transplantation, which remains as a dangerous procedure with many possible complications with mortality of 30%. Side effects related to transplantation can also be short-term, lasting from weeks to months, or long-term that can last years or a lifetime.

Despite advances in our understanding of the molecular biology of AML and although in up to half of the patients complete remission occurs, for many patients relapse is generally expected and prognosis is dismal. Current clinical challenge is thus to better stratify AML patients according to their expected prognosis. Especially it would be useful to develop more sensitive diagnostic methods for the detection of those patients that with current risk group classification are determined as favourable prognosis patient but which cannot be cured with standard chemotherapy but should be directed immediately to stem cell transplantation.

Thus new clinical and molecular markers for AML prognosis and minimal residual disease monitoring are needed. As part of routine clinical diagnostics, AML patient samples are examined with PCR for fusion genes and mutations that are characteristic for AML. However, not all of the genetic abnormalities behind the WHO classification of AML for poor prognosis are known, and actually only for half of the AML patients there is a relevant molecular genetic PCR test available. Thus, there is a clear medical need to identify new genetic changes that could be used to design and optimize treatment strategies for AML patients.

Protein Phosphatase 2A (PP2A) is a trimeric (A-B-C subunits) tumor suppressor complex. In cancer cells, the tumor suppressor activity of PP2A is inhibited. However, the PP2A complex proteins are mutated with rather low frequency in all cancer types. Instead, the most prevalent mode of PP2A inhibition in cancer seems to be the overexpression of PP2A inhibitor proteins, such as CIP2A, SET and PME1. CIP2A overexpression associates with poor patient prognosis in more than dozen human solid cancer types (Khanna and Pimanda, 2015). SET is known to be overexpressed in human AML (Cristóbal I et al, 2010).

Further markers for prognosing cancer, including lymphoid cancers such as AML, are still needed.

BRIEF DESCRIPTION OF THE INVENTION

An object of the present invention is to provide means and methods for various aspects of cancer diagnostics and prognostics. This object is achieved by arrangements which are characterized by what is stated in the independent claims. Some preferred embodiments are disclosed in the dependent claims.

The invention is, at least partly, based on studies revealing that cancer cells may express different isoforms of CIP2A with potentially different functions. A novel isoform of CIP2A is identified.

Thus, in one aspect, the invention provides an isolated polypeptide variant of CIP2A, named NOCIVA, comprising an amino acid sequence set forth in SEQ ID NO: 3. In some embodiments, said polypeptide comprises at least part of an amino acid sequence set forth in SEQ ID NO: 2, or comprises or consists of an amino acid sequence having at least 80% sequence identity with SEQ ID NO: 2 outside the region formed by amino acids 546-558. In some further embodiments, the polypeptide is encoded by a polynucleotide comprising the nucleic acid sequence defined by nucleotides 1636-1674 of SEQ ID NO: 1, or comprising exons 1-13 of CIP2A C-terminally attached in frame to part of intron 13 of CIP2A. In some even further embodiments, the polypeptide is encoded by a polynucleotide comprising or consisting of a nucleic acid sequence set forth in SEQ ID NO: 1 or a nucleic acid sequence having at least 80% sequence identity with SEQ ID NO: 1 outside the region defined by nucleotides 1636-1674 of SEQ ID NO: 1.

In another aspect, the invention provides an isolated CIP2A polynucleotide variant, preferably cDNA variant, encoding the polypeptide of the invention. In some embodiments, the polynucleotide comprises a nucleic acid sequence defined by nucleotides 1636-1674 of SEQ ID NO: 1. In some further embodiments, the polynucleotide comprises exons 1-13 of CIP2A C-terminally attached in frame to part of intron 13 of CIP2A. In some still further embodiments, the polynucleotide further comprises 3'UTR. In some even further embodiments, the polynucleotide comprises at least part of a nucleic acid sequence set forth in SEQ ID NO: 1, or comprises or consists of a nucleic acid sequence having at least 80% sequence identity with SEQ ID NO: 1 outside the region defined by nucleotides 1636-1674 of SEQ ID NO: 1.

Also provided is use of the present polypeptides or polynucleotide as cancer biomarkers. In some embodiments, said cancer is selected from the group consisting of lymphoid cancers and solid cancers. In some further embodiments, said lymphoid cancer is selected from the group consisting of acute myeloid leukaemia (AML) and chronic myeloid leukaemia (CML); while solid cancer is selected from the group consisting of squamous cell carcinoma (SCC), head and neck squamous cell carcinoma (HNSCC), lung cancer, breast cancer, colorectum cancer, prostate cancer, stomach cancer, liver cancer, cervix uteri cancer, oesophagus, bladder cancer, kidney cancer, and pancreatic cancer.

In a further aspect, the invention provides an anti-CIP2A variant antibody, i.e. an anti-NOCIVA antibody, or an antigen-binding fragment thereof which specifically binds to the polypeptide according to the invention.

In a still further aspect, the invention provides an oligonucleotide, such as a probe, which hybridizes specifically with the polynucleotide according to the invention. In some embodiments, the oligonucleotide hybridizes specifically with a target sequence, which is encompassed by or overlaps with a sequence formed by nucleotides 1635-1983 of SEQ ID NO: 1. In some further embodiments, the oligonucleotide hybridizes with 8-40, preferably 15-35, more preferably 20-30 consecutive nucleotides of a sequence formed by nucleotides 1635-1983, 1636-1674, or 1675-1983 of SEQ ID NO: 1.

In an even further aspect, the invention provides a primer pair which specifically amplifies at least a part of the polynucleotide according to the invention. In some embodiments, the primer pair comprises a 3'-primer which specifically hybridizes with a target sequence encompassed by or overlapping with a sequence formed by nucleotides 1635-1983, 1636-1674, or 1675-1983 of SEQ ID NO: 1. In some embodiments, the primer pair comprises a 5'-primer which specifically hybridizes with a target sequence encompassed by a sequence formed by nucleotides 1 to 1634 of SEQ ID NO: 1.

Also provided is a method for prognosing, detecting, screening, diagnosing, or monitoring cancer. Said method comprises determining the expression level of the polypeptide or polynucleotide according to the invention in a sample from a subject. The method may in some embodiments involve nucleic acid amplification, e.g. by a primer pair according to the invention, and/or hybridizing the present polynucleotide with an oligonucleotide according to the invention. Alternatively, the method may involve using an antibody according to the invention. The method may also be implemented using a technique selected from the group consisting of next generation sequencing, RNA in situ hybridization, and targeted quantitative proteomics by mass spectrometry such as selected reaction monitoring (SRM), SWATH and mass cytometry, for example.

In one aspect, the invention provides a method of assigning treatment to a subject diagnosed with AML. The method comprises the steps of: contacting a biological sample from the subject with a reagent that specifically binds to a polypeptide or polynucleotide according to the invention; determining the expression level of said polypeptide or said polynucleotide based on said binding; determining whether or not the determined expression level of said polypeptide or said polynucleotide is increased in the sample by comparing said expression level to a control; and assigning a treatment regime comprising stem cell therapy if said expression is increased.

In a further aspect, the invention provides an immunoassay for detecting the presence of the polypeptide according to the invention in a clinical sample. The immunoassay comprises contacting the sample with the antibody according to the invention; and detecting specific binding of the antibody, if any, qualitatively or quantitatively.

In still further aspect, the invention provides a method for detecting the presence of the polynucleotide according to the invention in a biological sample. The method comprises: a) contacting the sample with an oligonucleotide according to the invention; and b) detecting specific hybridization of the oligonucleotide. In some embodiments, the method may comprise prior to a), amplifying said polynucleotide using a primer pair according to the invention.

In an even further aspect, the invention provides a method for detecting the presence of the polynucleotide according to the invention in a biological sample. The method comprises: a) contacting the sample with a primer pair according to the invention; b) performing nucleic acid amplification; and c) detecting the amplicon obtained in step b) qualitatively or quantitatively with the oligonucleotide according to the invention.

Also provide is a kit for determining the level of the polypeptide according to the invention, wherein the kit comprises an antibody according to the invention; and a kit for determining the level of the polynucleotide according to the invention, wherein the kit comprises an oligonucleotide according to the invention and/or the primer pair according to the invention.

Other objectives, aspects, embodiments, details and advantages of the present invention will become apparent from the following figures, detailed description, examples, and dependent claims.

BRIEF DESCRIPTION OF THE DRAWINGS

In the following the invention will be described in greater detail by means of preferred embodiments with reference to the attached drawings, in which FIGS. 1A to 1D illustrate identification of novel CIP2A mRNA variants.

FIG. 1A is a schematic presentation of CIP2A mRNA isoforms identified with RACE-PCR. Three CIP2A mRNA variants were found. NOCIVA mRNA contains an alternative exon from CIP2A intron number 13, and thus forms a unique and previously unknown coding sequence. Untranslated region (5'UTR or 3'UTR) is marked with dots, unique alternative exon in NOCIVA with vertical lining and NOCIVA specific 3'UTR with grey gradient and dashed stroke.

FIG. 1B illustrates NOCIVA mRNA's 3'-end with the differing features from the original CIP2A mRNA sequence. Shared nucleotide sequence between CIP2A and NOCIVA mRNA is underlined. NOCIVA protein comprises 545 N-terminal CIP2A amino acids and 13 unique amino acids on the C-terminus (bolded). The stop codon is indicated by an asterisk. NOCIVA mRNA contains also 3'UTR (1675-2010 of SEQ ID NO: 1) and polyadenylation signal (AATAAA at 1962-1967 of SEQ ID NO: 1). Polyadenylation signal and poly(A) tail are marked with boxes. Shown is a partial nucleic acid sequence of SEQ ID NO: 1 and a partial amino acid sequence of SEQ ID NO: 2.

FIG. 1C shows results of confirmation RT-PCR to validate NOCIVA specific mRNA sequence expression from several cell lines. NTC stands for non-template control. Resulting bands were extracted and presence of specific NOCIVA mRNA was confirmed by sequencing.

FIG. 1D illustrates NOCIVA mRNA formation from KIAA1524 gene and shows a part of the nucleic acid sequence of KIAA1524 (SEQ ID NO: 89). CIP2A exon13 and exon14 are marked with underlining. Regular text is used for intronic sequence between exons 13 and 14. Bolded is the intronic region of which NOCIVA mRNA is produced (corresponding to nucleotides 1635-1983 in SEQ ID NO: 1). Bolded sequence is as well a part of intronic sequence between exons 13 and 14.

FIG. 2A demonstrates NOCIVA mRNA expression measured by qPCR with two different primer-probe-sets in patient derived keratinosyte (Ker) and squamous cell carcinoma (SCC) cells. b-actin & GAPDH were used as housekeeping genes and mRNA expression levels in Ker 45B cells was defined as value 1.

FIG. 2B shows NOCIVA, CIP2Ae13 (i.e. CIP2A determined by using a 5'primer hybridizing to exon 13 and a 3'primer hybridizing to exon 14) and CIP2Ae20 (i.e. CIP2A determined by using a 5'primer hybridizing to exon 20 and a 3'primer hybridizing to exon 21) mRNA expression in normal tissue panel (Human MTC panel I & II, Clontech). b-actin & GAPDH were used as housekeeping genes.

FIG. 2C shows ratios of NOCIVA and CIP2Ae13 mRNA expressions in normal tissue samples from FIG. 2B.

FIG. 2D shows NOCIVA and CIP2Ae20 mRNA expression in indicated AML and CML cell lines. AML: Acute myeolid leukemia; CML: Chronic myeloid leukemia. Hela, UT-7 and MCF7 represent solid human cancers here.

FIG. 2E shows NOCIVA mRNA expression in patient derived diagnostic AML samples as compared with average expression in keratinocytes and SCC cells from FIG. 2A.

FIGS. 3A to 3B illustrate NOCIVA mRNA overexpression in diagnostic lymphoid samples.

FIG. 3A is a waterfall blot displaying distribution of 93 diagnostic human AML samples with either overexpression or underexpression of CIP2A or NOCIVA mRNA as compared to normal bone marrow sample defined as zero value. b-actin and GAPDH were used as housekeeping genes.

FIG. 3B shows the percentage of 93 diagnostic AML patient samples displaying overexpression of the indicated genes as compared to normal bone marrow sample. FC>2: percentage of samples with overexpression more than twofold.

FIGS. 4A to 4F show statistics and clinical correlations of the AML patient material.

FIG. 4A shows distribution of the patient material with clinical follow-up information according to risk groups as defined under the table. Percent alive refers to living patients after follow-up time (03/17, median follow-up 5.4 years).

FIG. 4B shows the statistical correlation of patient diagnostic age and risk group to overall survival in a multivariate analysis.

FIG. 4C shows the correlation of the expression of indicated markers to risk group in the studied patient population. Neither CIP2A nor NOCIVA mRNA expression is statistically different between the risk groups (p-values shown in brackets).

FIG. 4D shows that high NOCIVA expression significantly associates with poor overall survival in a multivariant analysis.

FIG. 4E shows Kaplan-Meier plot of overall survival of AML patients according to NOCIVA expression levels divided to low or high. Median serves as a cut of value.

FIG. 4F shows that high NOCIVA/CIP2Ae13 ratio significantly associates with poor overall survival in a multivariate analysis.

DETAILED DESCRIPTION OF THE INVENTION

Figure 1A:
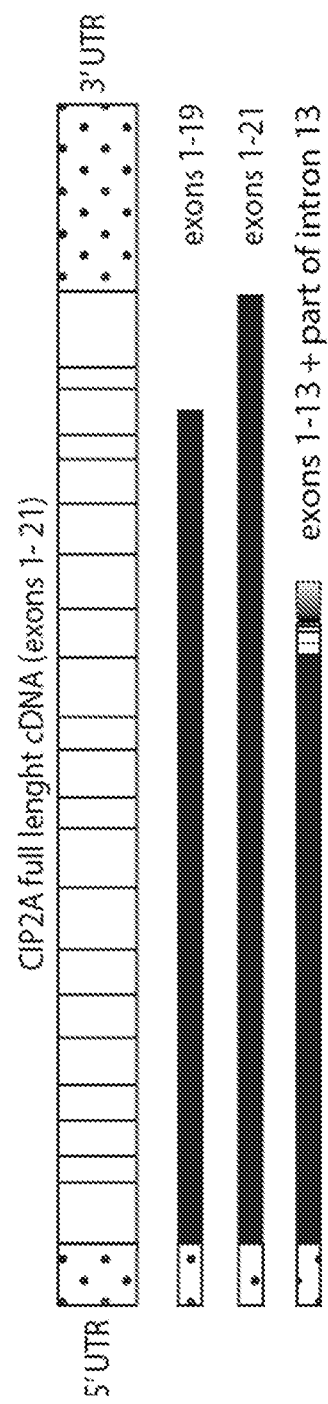

The present invention provides a novel variant of cancerous inhibitor of PP2A (CIP2A or KIAA1524), named as NOCIVA. At mRNA level, the variant comprises exons 1-13 of CIP2A fused C-terminally to a part of the intron between exons 13 and 14 in KIAA1524 gene. NOCIVA transcript thus formed is a unique and previously unknown sequence, wherein the intronic sequence is in a coding frame with a preceding CIP2A mRNA sequence, and after 40 nucleotides, corresponding to 13 amino acids, is followed by classical stop codon (translation termination) TAA. Three prime untranslated region (3'UTR) is the section of mRNA that immediately follows the translation termination codon and regulatory regions within the 3'UTR can influence polyadenylation, translation efficiency, localization, and stability of the mRNA. Potential 3'UTR of NOCIVA consists of approximately 350 nucleotides including the AATAAA sequence that directs addition of several adenine residues called the poly(A) tail to the end of the mRNA transcript. Thus, the NOCIVA gene product codes for a truncated CIP2A protein with 13 new amino acids (NNKNTQEAFQVTS; SEQ ID NO: 3) at the C-terminal end. Importantly, this 13 aa peptide sequence do not match with any known protein sequence in the human proteome based on a Blast homology search. The nucleic acid sequence set forth in SEQ ID NO: 1 represents the complementary DNA (cDNA) sequence of NOCIVA mRNA, while the amino acid sequence of NOCIVA polypeptide is set forth in SEQ ID NO: 2. SEQ ID NO: 3 corresponds to amino acids 546-558 of SEQ ID NO: 2. For the sake of clarity, the structures of interest in the NOCIVA mRNA sequence are indicated referring to the respective NOCIVA DNA/cDNA sequence of SEQ ID NO: 1.

The NOCIVA-specific mRNA (nucleotides 1635-2010 in the SEQ ID NO:1, length 376 nt) contains the following structures:

NOCIVA-specific intronic mRNA sequence without the poly-A tail: nucleotides 1635-1983 of SEQ ID NO:1 (350 nt);

NOCIVA mRNA sequence encoding the novel NOCIVA-peptide (13 amino acids): nucleotides 1636-1674 (39 nt) of SEQ ID NO: 1;

3' UTR: nucleotides 1675-2010 (335 nt) of SEQ ID NO: 1;

3'UTR without the poly-A tail: nucleotides 1675-1983 of SEQ ID NO: 1 (310 nt);

poly-A tail: nucleotides 1984-2010 of SEQ ID NO: 1; and polyadenylation signal: nucleotides 1962-1967 of SEQ ID NO: 1.

It should be noted that while the first nucleotide of the unique NOCIVA sequence (nucleotide 1635 in SEQ ID NO: 1) does not result in a change of the last amino acid preceeding the novel NOCIVA peptide, it is yet specific for the NOCIVA mRNA.

Also included are NOCIVA polypeptides and polynucleotides that have at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the sequences depicted in SEQ ID NOs:1-3, provided that they retain the functional properties of NOCIVA.

In view of the above, NOCIVA polypeptides and polypeptides encompass conservative sequence variants thereof. In connection with polypeptides, the term "conservative sequence variant" refers to amino acid sequence modifications, which arise from amino acid substitutions with similar amino acids well known in the art (e.g. amino acids of similar size and with similar charge properties) and which do not significantly alter the biological properties of the polypeptide in question. Amino acid deletions and additions are also contemplated. In connection with polynucleotides, the term "conservative sequence variant" refers to nucleotide sequence modifications, which do not significantly alter biological properties of the encoded polypeptide. Conservative nucleotide sequence variants include variants arising from the degeneration of the genetic code and from silent mutations. Nucleotide substitutions, deletions and additions are also contemplated.

As used herein, the percentage of sequence identity between two sequences is a function of the number of identical positions shared by the sequences (i.e. % identity=# of identical positions/total # of positions×100), taking into account the number of gaps, and the length of each gap, which need to be introduced for optimal alignment of the two sequences. The comparison of sequences and determination of identity percentage between two sequences can be accomplished using mathematical algorithms available in the art. This applies to both amino acid and nucleic acid sequences.

In some embodiments, the NOCIVA polypeptide comprises the amino acid sequence set forth in SEQ ID NO: 3. In some embodiments, the NOCIVA polypeptide comprises the amino acid sequence set forth in SEQ ID NO: 2 or a conservative sequence variant thereof. In some embodiments, the NOCIVA polypeptide may comprise an amino acid sequence having at least 80% sequence identity (or any other % sequence identity set forth above) with SEQ ID NO: 2 outside the region formed by amino acids 546-558. In other words, despite sequence variation, such NOCIVA variants still comprise the amino acid sequence set forth in SEQ ID NO: 3 (corresponding to amino acids 546-558 of SEQ ID NO: 2). Such NOCIVA variants should retain the functional properties of the NOCIVA polypeptide. Whether or not a certain NOCIVA variant has retained the functional properties of the NOCIVA polypeptide of SEQ ID NO: 2 can be carried out by routine experimentation.

In some embodiments, the NOCIVA polypeptide comprises the amino acid sequence set forth in SEQ ID NO: 3. In some embodiments, the NOCIVA polypeptide comprises the amino acid sequence set forth in SEQ ID NO: 2 or a conservative sequence variant thereof. In some embodiments, the NOCIVA polypeptide may comprise an amino acid sequence having at least 80% sequence identity (or any other % sequence identity set forth above) with SEQ ID NO: 2 outside the region formed by amino acids 546-558. In other words, despite sequence variation, such NOCIVA variants still comprise the amino acid sequence set forth in SEQ ID NO: 3 (corresponding to amino acids 546-558 of SEQ ID NO: 2). Such NOCIVA variants should retain the functional properties of the NOCIVA polypeptide. Whether or not a certain NOCIVA variant has retained the functional properties of the NOCIVA polypeptide of SEQ ID NO: 2 can be carried out by routine experimentation.

NOCIVA is expressed only at a very low level in normal human tissues but it is expressed in cells from various cancers, such as head and neck squamous cell carcinoma (HNSCC), acute myeloid leukaemia (AML) and chronic myeloid leukemia (CML). Thus, NOCIVA is a novel cancer-associated biomarker that can be utilized either at mRNA level or protein level. Although the present disclosure focuses on some lymphoid cancers, namely AML, CML and acute promyelocytic leukemia (APL), NOCIVA may be utilized not only as a marker of haematological cancesrs, such as leukaemias, but also as a marker for solid cancers as well, including but not limited to squamous cell carcinoma (SCC) such as HNSCC, lung cancer, breast cancer, colorectum cancer, prostate cancer, stomach cancer, liver cancer, cervix uteri cancer, oesophagus, bladder cancer, kidney cancer, and pancreatic cancer.

As used herein, the term "haematological cancer" refers to a malignancy affecting blood, bone marrow or lymph nodes. Haematological cancers are referred to as leukaemia, lymphoma and myeloma depending on the type of cell affected. Lymphoma is a group of blood cancers that develop from lymphocytes. Multiple myeloma, also known as plasma cell myeloma, is a cancer of plasma cells.

As used herein, the term "leukaemia" refers to a cancer which starts in blood-forming tissue, usually the bone marrow, and affects white blood cells. Leukaemia can be classified by the type of white cell affected (myeloid or lymphatic). Non-limiting examples of leukaemias include acute myeloid leukaemia (AML), chronic myeloid leukaemia (CML), acute promyelocytic leukemia (APL), and subgroups thereof.

As used herein, the terms "biomarker" and "marker" are interchangeable, and refer to a molecule which is differentially present in a sample taken from a subject with cancer as compared to a comparable sample take from a control subject, such as an apparently healthy subject or a subject with the same cancer but having a different prognosis of the disease.

Measurement of NOCIVA in patient samples provides information that can be correlated with a probable presence, absence, or prognosis of a suspected cancer or a subtype thereof. The measurement of NOCIVA can be performed prior to, simultaneously or following the assaying of other markers relevant to the suspected cancer type or a subtype thereof. This is also meant to include instances where the presence, absence, or prognosis of cancer, or a subtype thereof, is not finally determined but that further diagnostic testing is warranted. In such embodiments, the method is not by itself determinative of the presence, absence, or prognosis of cancer or a subtype thereof, but can indicate that further diagnostic testing is needed or would be beneficial. Therefore, NOCIVA may be used in combination with one or more other diagnostic methods or markers for the final determination of the presence, absence, or prognosis of said cancer or a subtype thereof. Such other diagnostic methods and markers are well known to a person skilled in the art. With respect to AML, such other markers include, but are not limited to, WT1, EVIL and SET.

Accordingly, NOCIVA may be used not only for diagnostic purposes but, for example, also for prognosis, prediction, patient grouping or stratification, monitoring cancer progression over time, monitoring any possible cancer remission, recurrence or relapse, therapy selection, and treatment monitoring.

As used herein, the term "prognosis" refers to a probable course or clinical outcome of a disease, while the expressions "prognosticating" and "prognosing" refer to a prediction of future course of the disease.

As used herein, the term "good prognosis" refers to a probable favourable course of the disease for a certain period of time. "Prolonged overall survival", "prolonged disease-free survival", "prolonged recurrence-free survival" and "prolonged progression-free survival", when compared to the median outcome of the disease for example, are non-limiting examples of good prognosis. Depending on the haematological cancer and embodiment in question, good prognosis may refer to, for example at least 20%, at least 30%, at least 40%, at least 50%, at least 60%, at least 70%, at least 80% or at least 90% chance of surviving more than 1 year, more than 2 years, more than 3 years, more than 4 years or more than 5 years after the diagnosis.

As used herein, term "poor prognosis" refers to a probable non-favourable course of the disease for a certain period of time. "Reduced overall survival", "reduced disease-free survival", "reduced recurrence-free survival" and "reduced progression-free survival", when compared to the median outcome of the disease for example, are non-limiting examples of poor prognosis. Depending on the haematological cancer and embodiment in question, poor prognosis may refer to, for example less than 60%, less than 50%, less than 40%, less than 30%, less than 20% or less than 10% a likelihood of surviving more than 1 year, more than 2 years, more than 3 years, more than 4 years or more than 5 years after the diagnosis.

Likelihood of a certain clinical outcome of a disease, such as likelihood of a poor prognosis in a subject diagnosed with haematological cancer, may be expressed as a probability, such as a "hazard ratio" (HR), which term refers to the ratio of an instantaneous risk in two experimental arms over the study time period. It represents point estimate at any given point of time.

Thus, with respect to poor prognosis, for example, if the HR risk estimate for a particular biomarker level is greater than one, this indicates that a subject with this particular biomarker level has a higher risk for poor prognosis than a subject without the particular biomarker level. In contrast, if the HR risk estimate for a particular biomarker level is less than one, this indicates that a subject with this particular biomarker level has a reduced risk for the poor prognosis as compared to a subject without the particular biomarker level.

As used herein, the term "95% confidence interval" (95% CI) refers to an estimated range of values that one can be 95% certain contains the true mean of the population, the estimated range being calculated from a given set of sample data. Generally, the 95% CI is used to estimate the precision of the HR. A wide CI indicates a low level of precision of the HR, whereas a narrow CI indicates a higher precision of the HR.

Multivariate analysis (Cox proportional hazards model) described herein revealed statistically significant associations between NOCIVA expression levels and clinical outcomes, such that patients with higher NOCIVA burden had lower overall survival times (p=0.0205, HR: 1.511; FIG. 4D) than patients with lower NOCIVA burden. Interestingly, no such association was observed with CIP2A. In fact, the HR risk estimate for overall survival when CIP2A was used as a biomarker level was less than one (p=0.0775, HR: 0.173; FIG. 4D), indicating reduced risk for the poor overall survival for patients with higher CIP2A burden than patients with lower CIP2A burden.

NOCIVA determinations may provide substantial help in clinical decision making in choosing appropriate treatment procedures especially because NOCIVA mRNA expression does not seem to be dependent on the AML risk group classification described for example in "Diagnosis and management of AML in adults: 2017 ELN recommendations from an international expert panel" by Hartmut Döhner and others. For example, increased expression of NOCIVA in a subject having AML indicates poor overall survival, and that it might be beneficial to direct such subjects to immediate stem cell transplantation, which is a treatment modality well known in the art. On the other hand, it would be sufficient to treat AML patients with non-increased expression of NOCIVA with chemotherapy only. Thus, NOCIVA may be used for stratifying subjects into groups of either poor prognosis or good prognosis, as well as stratifying subjects for different treatment modalities.

In accordance with the above, the present invention provides a method of assigning treatment to a subject diagnosed with AML, the method comprising the steps of: contacting a biological sample obtained from the subject with a reagent (such as a binding body provided herein) that specifically binds to the present NOCIVA polypeptide or polynucleotide; determining whether or not the expression of said polypeptide or said polynucleotide is increased in said sample by comparing said expression with a relevant control; and assigning a treatment regime comprising e.g. stem cell therapy, if said expression is increased.

The present invention provides advantages not only for individual patient care but also for better selection and stratification of patients for clinical trials. For example, cancer patients grouped on the basis of their NOCIVA expression levels could be employed in clinical studies with the aim of developing efficient new personalized therapeutic tools such as new medical procedures or drugs.

In accordance with the above, analyzing and predicting a response to treatment may be carried out in any of the following cohorts: a cohort that responds favourably to a treatment regimen, a cohort that does not respond favourable to a treatment regimen, a cohort that responds significantly to a treatment regimen, a cohort that does not respond significantly to a treatment regimen, and a cohort that responds adversely to a treatment regimen (e.g. exhibits one or more side effects). These cohorts are provided as examples only, and any other cohorts or sub-cohorts may be analysed. Thus, a subject may be determined for NOCIVA expression level to predict whether he/she will respond favourably or significantly to a treatment regiment, not respond favourably or significantly to a treatment regimen, or respond adversely to a treatment regimen. If a subject is likely to respond positively to a cancer treatment, said subject may be treated accordingly. On the other hand, if a subject is likely to respond negatively (i.e. not exhibit positive effects or exhibit adverse side effects) to a cancer treatment, an alternative course of treatment may be applied.

Accordingly, the present invention provides various methods or assays for the purposes set forth above. These methods or assays involve determination of NOCIVA expression level in a sample obtained from a subject in question. As used herein, the term "determining an expression level of NOCIVA", and any corresponding expressions, refer to quantifying or semi-quantifying NOCIVA either on the basis of mRNA, cDNA, or protein amount. The term "level" is interchangeable with the terms "amount" and "concentration", and can refer to an absolute or relative quantity. Determining NOCIVA expression may also include determining the absence or presence of NOCIVA qualitatively.

In some embodiments, relative expression level of NOCIVA may be based on the relative ratio of NOCIVA expression to the expression of a previously known CIP2A form, i.e. CIP2A with exons 1-21. The expression level of CIP2A may be determined, for example, on the basis of the expression level of exon 13 (CIP2Ae13), exon 16 (CIP2Ae16), or exon 20 (i.e. CIP2Ae20). Preferably, the relative expression ratio of NOCIVA to CIP2A is based on determining the expression levels of NOCIVA and CIP2A in the same cells. In some embodiments, CIP2Ae13 is determined by using a 5'primer hybridizing to exon 13 and a 3'primer hybridizing to exon 14; CIP2Ae16 is determined by using a 5'primer hybridizing to exon 16 and a 3'primer hybridizing to exon 17; while CIP2Ae20 is determined by using a 5'primer hybridizing to exon 20 and a 3'primer hybridizing to exon 21.

In some further embodiments, the expression level of NOCIVA may be determined as a relative ratio between the expression level of NOCIVA and that of an appropriate housekeeping gene, in the same cells. Non-limiting examples of suitable housekeeping genes include GAPDH (Glyceraldehyde-3-phosphate dehydrogenase), ACTB (Actin, beta), RRN18S (18S ribosomal RNA), PGK1 (Phosphoglycerate kinase 1), PPIA (Peptidylprolyl isomerase A (cyclophilin A)), RPL13A (Ribosomal protein L13a), RPLPO (Ribosomal protein, large, P0), B2M (Beta-2-microglobulin), YWHAZ (Tyrosine 3-monooxygenase/tryptophan 5-monooxygenase activation protein, zeta polypeptide), SDHA (Succinate dehydrogenase), TFRC (Transferrin receptor (p90, CD71)), ALAS1 (Amino-levulinate, delta-, synthase 1), GUSB (Glucuronidase, beta), HMBS (Hydroxy-methyl-bilane synthase), HPRT1 (Hypoxanthine phosphoribosyltransferase 1), TBP (TATA box binding protein), and TUBB (Tubulin, beta polypeptide). In some embodiments, preferred housekeeping genes include GAPDH and ACTB.

To determine whether a detected NOCIVA expression level is indicative of a cancer or a prognosis thereof, it should be compared with a relevant control. Once the control level is known, the determined or detected NOCIVA level can be compared therewith and the significance of the difference can be assessed using standard statistical methods. In some embodiments, a statistically significant difference between the determined NOCIVA level and the control level is indicative of the presence of cancer or a subgroup thereof (e.g. a subgroup on the basis of prognosis or expected response to treatment). In some further embodiments, before to be compared with the control, the NOCIVA levels are normalized using standard methods.

As used herein, the term "control" may refer to many different types of controls. For example, "negative control" or "normal control" means the control level of NOCIVA, alone or in comparison with another marker or control, determined from a non-cancerous tissue of the same subject, or from a sample obtained from an apparently healthy individual or a pool of apparently healthy individuals. "Positive control" may mean, for example, cancerous tissue of the same subject, or a sample obtained from an individual diagnosed with the cancer of interest, or a pool of individuals diagnosed earlier with cancer. A predetermined threshold value that is indicative of the presence, absence or prognosis of a cancer in question or a subgroup thereof may also be employed as a control, i.e. "threshold control". Accordingly, the threshold value may be a negative control value obtained from a pool of apparently heathy individuals, wherein the value refers to expression levels of NOCIVA in normal, non-cancerous cells; or it may be a positive control value, obtained from a pool of individuals with cancer, wherein the value refers to an expression level of NOCIVA in cancerous tissues.

"Internal control" may refer to an expression level of CIP2A and/or an expression level of one or more appropriate housekeeping genes determined from the same cells as the expression level of NOCIVA. In other words, the internal control may mean a loading control which allows quantifying NOCIVA in the sample being analyzed. Examples for an internal control, in other words "loading control" or "quantifying control" include housekeeping genes and housekeeping proteins. The quantity of NOCIVA may also be measured relative to a "control biomarker" such as another form of CIP2A. "Control ratio" means the relationship of NOCIVA to any selected control, for example the ratio between NOCIVA and another form of CIP2A.

In some preferred embodiments, another form of CIP2A, such as CIP2Ae20, is employed as a control so that the determined expression level of NOCIVA is compared with the determined expression level of CIP2Ae20 to obtain a ratio of NOCIVA expression to CIP2Ae20 expression. Said obtained ratio is then compared with said predetermined threshold to deduce the cancer status of the patient.

Statistical methods for determining appropriate control or threshold values will be readily apparent to those of ordinary skill in the art. The control or threshold values may have been determined, if necessary, from samples of subjects of the same age group, demographic features, and/or disease status, etc. The negative control or threshold value may originate from a single individual not affected by a cancer in question or a subtype thereof, or be a value pooled from more than one such individual.

As used herein, the term "apparently healthy" refers to an individual or a pool of individuals who show no signs of a cancer or its subtype in question, and thus are believed not to be affected by said cancer or its subtype in question and/or who are predicted not to develop said cancer or its subtype in question.

As used herein, the term "subject" refers to an animal, preferably to a mammal, more preferably to a human. The term includes, but is not limited to, mammalian animals such as domestic animals such as livestock, pets and sporting animals. Examples of such animals include without limitation carnivores such as cats and dogs and ungulates such as horses. Thus, the present invention may be applied in both human and veterinary medicine. Herein, the terms "subject", "patient" and "individual" are interchangeable.

As used herein, the term "sample" refers to a biological or clinical sample obtained from a subject whose NOCIVA expression level is to be determined. Typically, the sample is a sample of a cancerous tissue or a tissue suspected of being cancerous. In case of haematological cancers, such as leukemias, the sample may be a blood sample or a bone marrow sample obtained e.g. by a biopsy or aspiration. The sample may also be a paraffin embedded tissue sample. Examples of blood samples include whole blood samples, serum samples, plasma samples, samples of fractionated or non-fractionated peripheral blood mononuclear cells (PBMCs) or samples of other purified blood cell types.

The term "sample" also includes samples that have been manipulated or treated in any appropriate way after their procurement, including but not limited to centrifugation, filtration, precipitation, dialysis, chromatography, treatment with reagents, washing, or enriching for a certain component of the sample such as a cell population.

As used herein, the term "increased expression" refers to an increase in the amount of a biomarker in a sample as compared with a relevant control. Said increase can be determined qualitatively and/or quantitatively according to standard methods known in the art. The expression is increased if the amount or level of the biomarker in the sample is, for instance, at least about 1.5 times, 1.75 times, 2 times, 3 times, 4 times, 5 times, 6 times, 8 times, 9 times, time times, 10 times, 20 times or 30 times the control value or the amount of the same biomarker (NOCIVA) or a control biomarker (e.g. CIP2A or a housekeeping gene) in the control sample. In some embodiments, the term "increased expression" refers to a statistically significant increase in the level or amount of the biomarker as compared with that of a relevant, preferably negative, control. Increased expression as compared with a negative control indicates that the subject has or is at increased risk of having poor prognosis.

As used herein, the term "non-increased expression" refers to an expression level of a biomarker that is essentially the same both in a sample to be analyzed and in a relevant control. Non-increased expression as compared with a negative control indicates that the subject does not have or is not at risk of having poor prognosis.

As used herein, the term "decreased expression" refers to a decrease in the amount of a biomarker in a sample as compared with a relevant control. Said decrease can be determined qualitatively and/or quantitatively according to standard methods known in the art. The expression is decreased if the amount or level of the biomarker in the sample is, for instance, at least about 1.5 times, 1.75 times, 2 times, 3 times, 4 times, 5 times, 6 times, 8 times, 9 times, time times, 10 times, 20 times or 30 times lower that the control value or the amount of the same biomarker or a control biomarker (e.g. CIP2A or a housekeeping gene) in the control sample. In some embodiments, the term "decreased expression" refers to a statistically significant decrease in the level or amount of the biomarker as compared with that of a relevant control. Decreased expression as compared with a positive control may indicate that the subject does not have or is not at risk of having poor prognosis.

Determining the expression level of NOCIVA in a sample obtained from a subject who is to be diagnosed for cancer, prognosed for cancer, monitored for cancer progression, monitored for any possible cancer remission, recurrence or relapse, subjected to therapy selection, monitored for response to treatment, or grouped or stratified for any relevant cancer-related purpose can be determined by any available or future means suitable for this purpose. Said determination may be executed at different molecular levels, preferably at mRNA, cDNA, or protein level as is well known in the art. The present invention is not limited to any determination technique. Thus, in different embodiments, different means or combinations thereof for analyzing a biological or clinical sample for the expression of NOCIVA may be used.

In one aspect, the present invention provides an anti-NOCIVA antibody that specifically recognizes NOCIVA but does not recognize any other form of CIP2A, i.e. CIP2A polypeptide encoded by a CIP2A mRNA comprising exons surpassing exon 13. Accordingly, preferred epitopes for the present anti-NOCIVA antibodies include polypeptides that contain 5 to 20 consecutive amino acids of a sequence corresponding to or overlapping with a sequence formed by amino acids 546-558 of SEQ ID NO: 2.

The provided antibody may be, for example, a polyclonal antibody, a monoclonal antibody, a chimeric antibody, a humanized antibody, a human antibody, a recombinant antibody, a single chain antibody, or a functional antibody fragment, such as Fab, Fab', F(ab')2, or Fv, all of which are encompassed by the term "antibody".

Anti-NOCIVA antibodies according to the invention may be obtained by a variety techniques or any appropriate combination thereof. For example, the antibodies may be produced by traditional immunization methods, CDR grafting, in vitro protein expression, cell-free protein expression, cell-free translation, or cell-free protein synthesis, or obtained from a recombinant expression library, e.g. by employing a phage display based strategy. Functional antibody fragments and single-chain antibodies may be produced by recombinant DNA techniques, or by enzymatic or chemical separation of intact immunoglobulins as is well known in the art.

In some embodiments, the present anti-NOCIVA antibody may be conjugated or otherwise attached with, or produced as a fusion to, one or more peptide or small protein tags that facilitate purification, isolation, immobilization and/or detection. Non-limiting examples of suitable affinity tags for purification or immobilization purposes include polyhistidine tags (His-tags), hemagglutinin tags (HA-tags), glutathione-S-transferase tags (GST-tags), and biotin tags. Suitable detection tags include fluorescent proteins, such as GFP, and enzyme tags that will generate a colored product upon contact with a chromogenic substrate. Non-limiting examples of suitable enzyme tags include alkaline phosphatase (AP), and (horseradish) hydrogen peroxidase (HRP). Also other tags such as biotin, avidin, and streptavidin may be employed for detection purposes. They can be detected with a biotin/avidin/streptavidin-binding protein that is conjugated to an enzyme, fluorophore or other reporter molecule. Means and methods for producing such detectable and/or immobilizable anti-NOCIVA antibodies are readily available in the art.

The present anti-NOCIVA antibodies may be used for detecting NOCIVA expression at protein level for any purpose set for above. This may be accomplished by employing any suitable technique available in the art, including but not limited to methods and assays described below. Since NOCIVA is an intracellular protein, said methods and assays may comprise lyzing or disrupting cells, permeabilizing cell membranes, or isolating proteins according to means and methods well known in the art.

Generally, determining the level of NOCIVA expression at protein level comprises contacting a sample obtained from a subject in need of said determination with a binding body, such as an antibody, specifically recognizing NOCIVA polypeptide under conditions wherein the binding body specifically interacts with NOCIVA but not with full-length CIP2A whose amino acid sequence is set forth in SEQ ID NO: 4; and detecting said interaction (if any); wherein the presence or degree of said interaction correlates with the presence of NOCIVA or the level of NOCIVA expression in said sample. Binding bodies alternative to antibodies and fragments thereof suitable for determining NOCIVA expression at protein level include but are not limited to oligonucleotide or peptide aptamers, receptors and biologically interacting proteins.

Accordingly, in some embodiments the present invention provides an immunoassay for detecting and analyzing NOCIVA expression in a biological or clinical sample, wherein the immunoassay comprises: providing an antibody that specifically binds to NOCIVA; contacting a sample, preferably comprising permeabilized or disrupted cells, with the antibody; and detecting the presence of a complex of the antibody bound to NOCIVA in the sample. If desired, the antibody can be fixed to a solid support to facilitate washing and subsequent detection of the complex, prior to contacting the antibody with a sample. After incubating the sample with an anti-NOCIVA antibody, the mixture may be washed and the antibody-NOCIVA complex formed can be detected. This can be accomplished by e.g. using a detectable antibody, i.e., detectably labeled antibody, or an antibody labelled with an enzyme and incubating the complex with a detection reagent, i.e. substrate of the enzyme. Alternatively, NOCIVA can be detected using an indirect assay, wherein, for example, a second, labeled antibody is used to detect the antibody-NOCIVA complex formed.

In some embodiments, the expression level of NOCIVA may be determined using a non-competitive assay format. Non-competitive immunoassays, also known as reagent excess assays, sandwich assays, immunometric assays or two-site assays, generally involve use of two antibodies targeting different epitopes in the antigen, one antibody for antigen capture and the other labeled for detection. Preferably, the first antibody is the present anti-NOCIVA antibody, while the second antibody is a one that targets an epitope within a sequence formed by amino acids 1-545 of SEQ ID NO: 2. Such a second antibody specifically binds to both CIP2A and to NOCIVA. In some embodiments, the first antibody is employed as the capturing antibody, while the second antibody is employed as the detection antibody. In some other embodiments, the first antibody is employed as the detection antibody, while the second antibody is employed as the capturing antibody. A person skilled in the art will be well capable of establishing a binding assay for measuring the presence, absence or level of NOCIVA alone or in relation with another form of CIP2A or any other control. Accordingly, formation of the antibody-NOCIVA complex may be determined using any of a number of well-recognized non-competitive immunological binding assays. Useful assays include, for example, enzyme immune assays (EIA) such as enzyme-linked immunosorbent assay (ELISA); fluorescent immunosorbent assays (FIA) such as time-resolved immunoflurometric assays (TR-IFMA); chemiluminescence immunoassays (CLIA) and radioimmune assays (RIA).

Depending on the assay type employed, either the first antibody or the second antibody, or both, may be conjugated or otherwise associated with a detectable label selected from the group including, but not limited to, optical agents such as fluorescent labels including a variety of organic and/or inorganic small molecules and a variety of fluorescent proteins and derivatives thereof, phosphorescent labels, chemiluminescent labels, and chromogenic labels; radioactive labels such as radionuclides that emit gamma rays, positrons, beta or alpha particles, or X-rays, and enzymes such as alkaline phosphatase (AP) and (horseradish) hydrogen peroxidase (HRP). Said association can be direct, e.g. through a covalent bond, or indirect, e.g. via a secondary binding agent, a chelator, or a linker. Techniques for conjugating or otherwise associating detectable agents to antibodies are well known and antibody labelling kits are commercially available from dozens of sources. One or both of the antibodies may also be expressed as fusion proteins with a detectable label or a detection tag by recombinant techniques.

In some embodiments of non-competitive immunoassays, the detection antibody is detectably labelled. In some other embodiments, the detection antibody is recognized by a further antibody comprising a detectable label. In some still other embodiments, the detection antibody comprises a tag that is recognizable by a further antibody comprising a detectable label. In some still further embodiments, the detection antibody and said further antibodies are labelled with the same label, e.g. for improving sensitivity. In some other embodiments, the detection antibody and said further antibodies are labeled with different labels.

Immunoassays according to the present invention include solid-phase immunoassays, such as lateral flow assays and conventional sandwich assays carried out on a solid surface such as glass, plastic, ceramic, metal or a fibrous or porous material such as paper, in the form of e.g. a microtiter plate, a stick, a card, an array, a sensor, a bead, or a microbead. Said solid-phase immunoassay may be either heterogeneous or homogeneous. In heterogeneous assays, any free antigens or antibodies are physically separated from immunocomplexes formed, e.g. by washings, while no such separation is necessary in homogeneous assays including the many forms of biosensors.

The present homogeneous immunoassays are not limited to solid-phase assay formats but encompass also homogeneous immunoassays carried out in solution. Such in-solution immunoassays are particularly advantageous because neither immobilization nor washing steps are required, making them simple and easy to perform. Thus, in some embodiments, the immunoassay is liquid-based homogeneous immunoassay.

Any of the immunoassays mentioned above may be used in combination with a further immunoassay for determining the expression level of another form of CIP2A in the same sample. In such embodiments, the determined expression level of NOCIVA is compared with the determined expression level of CIP2A to obtain a ratio of NOCIVA expression to CIP2A expression. Determining said ratio may be used for any purpose set forth above. In some embodiments, increased ratio of NOCIVA to CIP2A as compared with that of a relevant control is indicative of poor prognosis.

Suitable antibodies for the above-mentioned purpose include those that specifically recognize CIP2A but do not specifically recognize NOCIVA. The epitope of such antibodies resides C-terminally to exon 13. In other words, the epitope resides between amino acids 546 and 905 of SEQ ID NO: 4. When the expression level of CIP2A is to be determined by a non-competitive immunoassay, a second antibody to be employed may be a one that targets the amino acid region 1-545 of SEQ ID NO: 4 (corresponding to the amino acid region 1-545 of NOCIVA, SEQ ID NO: 2). Such a second antibody specifically binds both to CIP2A and NOCIVA.

Further examples of suitable methods for determining the expression level of NOCIVA at protein level include conventional Western blot assays, dot blot assays and assay formats based on immunohistochemistry. Moreover, for example flow cytometry, such as fluorescence-activated cell sorting (FACS), may be used for detecting antibody-NOCIVA complexes. Moreover, techniques suitable for determining the expression level of NOCIVA at protein level include MS-based detection methods, such as selected reaction monitoring (SRM), SWATH and mass cytometry from cancer cell samples based on the unique peptide. Also in such embodiments, the method may include comparing the expression level of NOCIVA with that of CIP2A.

In a further aspect, the present invention provides nucleic acid binding bodies for use in determining NOCIVA expression at nucleic acid level, for example by the methods disclosed herein. Such binding bodies include probes specific for NOCIVA mRNA or cDNA, as well as primes for specific amplification of NOCIVA.

The regions especially suitable for determining the expression of NOCIVA at nucleic acid level include the NOCIVA-specific sequence without the poly-A tail (nucleotides 1635-1983 of SEQ ID NO: 1); the sequence encoding the novel NOCIVA peptide (nucleotides 1636-1674 of SEQ ID NO: 1); and the 3'UTR without the poly-A tail (nucleotides 1675-1983 of SEQ ID NO: 1).

One preferred embodiment for determining the presence/absence and/or quantity of NOCIVA-mRNA comprises the steps of:

a) providing a biological sample obtained from a subject and suspected to contain NOCIVA mRNA;

b) optionally performing reverse transcription of the mRNA to cDNA using, for example, random or poly-T primers or sequence-specific primers;

c) optionally amplifying NOCIVA specific DNA in said sample, if any; and d) detecting the NOVICA-specific sequence, such as mRNA, cDNA or amplified DNA with any selected method suitable for said task, wherein steps c) and d) may be performed either separately or simultaneously.

Owing to the sequence of NOCIVA mRNA, which is in most parts unique compared to other human mRNA, many alternative oligonucleotide designs can be employed in the present method. A person skilled in the art can easily design assays that are specific for NOCIVA or, for example, capable of separating and/or quantifying NOCIVA and some other form of CIP2A.

Applicable methods employing such oligonucleotides, particularly probes, include microarrays, which are a collection of nucleic acid, e.g. DNA spots attached to a solid surface. Each DNA spot contains an oligonucleotide of a specific DNA sequence, known as a probe or capture probe. These can consist of a short section of a gene or other oligonucleotide such as DNA or LNA element that are used to hybridize target cDNA, mRNA or cRNA (also called anti-sense RNA) in a sample under high-stringency conditions. Probe-target hybridization can be detected and/or quantified e.g. by detection of fluorophore-, silver-, or chemiluminescence-labeled target nucleic acids to determine their relative abundance in the sample. In some array types a recognition element (transducer) capable of converting a surface-bound probe-target nucleic acid interaction into a quantifiable signal may be incorporated. Among the several different types of transducers available, especially those based on electrochemical or optical detection are popular in the art. Similarly to other nucleic acid analysis methods, both types of sensors can either be run as label-free or label-using and also divided to heterogeneous and homogeneous assay formats based on the requirement for washing.

One suitable application is the NanoString's nCounter technology, which is a variation on the DNA microarray. It uses molecular "barcodes" and microscopic imaging to detect and count up to several hundred unique transcripts in one hybridization reaction. Each color-coded barcode is attached to a single target-specific probe corresponding to a gene of interest. In some embodiments the use of an array based technology such as the NanoString is beneficial in order to detect NOCIVA expression. Any polynucleotides or oligonucleotides described herein as probes may in other embodiments be used as primers, and vice versa. More generally, the present invention provides polynucleotides or oligonucleotides that are hybridisable with NOCIVA polynucleotide, i.e. polynucleotides or oligonucleotides that are complementary to NOCIVA mRNA or cDNA. The present NOCIVA-specific binding bodies may be designed as is well known in the art and as exemplified in FIG. 6 and Table 2. Non-limiting examples of probes suitable for detecting NOCIVA include probes comprising or consisting of a sequence set forth in SEQ ID Nos: 26-44.

The present NOCIVA-specific oligonucleotides can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies.

The present invention also concerns complementary sequences of the nucleic acid binding bodies or the target nucleic acid sequences disclosed herein. The term "complementary" is well known in the art and it means Watson-Crick base pairing where nucleobase adenine (A) in a target motif sequence is represented by nucleobase thymine (T) in a corresponding binding unit, or vice versa. Accordingly, nucleobase cytosine (C) in a target motif is represented by nucleobase guanine (G) in a corresponding binding unit, or vice versa. In other words, the complementary sequence to, for instance, 5'-T-T-C-A-G-3' is 3'-A-A-G-T-C-5'.

In some embodiments, the nucleic acid binding body provided herein is a primer. As used herein, the term "primer" refers to an oligonucleotide which is capable of annealing to (hybridizing with) a target sequence, thereby creating a double stranded region which can serve as an initiation point for DNA synthesis under suitable conditions. As used herein, the term "primer pair" refers herein to a pair of oligonucleotides, which are used together in amplifying a selected nucleic acid sequence by any available amplification technique, preferably polymerase chain reaction (PCR). Preferably, reverse transcription PCR (RT-PCR) is to be carried out on an mRNA sample. Other types of amplification processes include, but are not limited to, ligase chain reaction (LCR), strand displacement amplification (SDA), nucleic acid sequence-based amplification, transcription mediated amplification, signal mediated amplification of RNA technology, rolling circle amplification, loop-mediated amplification, multiple displacement amplification, helicase-dependent amplification, single primer isothermal amplification, or circular helicase-dependent amplification. As commonly known in the art, the primers are designed to bind to their complementary sequences under selected conditions. A primer pair contains a 5'-primer, i.e. a "forward primer", and a 3'-primer, i.e. a "reverse primer".

The present oligonucleotide primers may be of any suitable length, depending on the particular assay format employed. Typically, the oligonucleotide primers have a length of 10-40, preferably 15-35, and more preferably 20-30 nucleotides, and they may be adapted to be especially suited to a chosen nucleic acid amplification system. As commonly known in the art, the oligonucleotide primers can be designed by taking into consideration the melting point (i.e., melting temperature, Tm) of hybridization thereof with its targeted sequence. Many methods exist for increasing the melting temperature so that sufficiently high melting temperatures are achieved even with very short oligonucleotides. These methods include, for example, the use of modified nucleotides such as locked nucleic acid (LNA) or the minor groove binder (MGB) technology.

There are several ways to provide NOCIVA specificity in a nucleic acid assay. In some embodiments using at least two primers, such as PCR, at least the 3'-primer is designed to anneal to or hybridize specifically with at least part of the sequence encoding the unique C-terminal region of NOCIVA protein, i.e. the peptide-encoding intronic region formed by nucleotides 1635-1674 of SEQ ID NO: 1, so that the production of a NOCIVA-specific amplicon is brought about only when the peptide-encoding region is present in the sample Alternatively, similar specificity is achieved when the 3'-primer is designed specific for another site of the full-length NOCIVA-specific nucleic acid (without poly-A tail) or the 3'UTR of NOCIVA, i.e. it may anneal or hybridize specifically with at least part of a sequence formed by or overlapping with nucleotides 1635-1983 or 1675-1983 of SEQ ID NO: 1. This is because, although not present in the protein, the nucleotide sequence of the NOCIVA mRNA is in most parts unique to NOCIVA. Alternatively, the 3'-primer may also anneal or hybridize specifically with a sequence of SEQ ID NO: 1 that overlaps with the boundary of the peptide-encoding region and the 3'UTR of NOCIVA. In other words, the 3'-primer hybridizes to a target region encompassed by or residing within, or overlapping with a sequence formed by nucleotides 1675-1983 of SEQ ID NO: 1. In this connection, the term "encompassed by" means that the primer does not hybridize with the whole sequence formed by said nucleotides, but to a subsequence thereof, which subsequence corresponds to the target sequence. This definition applies not only to primers but also to other binding bodies such as probes.

Since it is sufficient that the NOCIVA-specificity of the primer pair is provided by the 3'-primer, the annealing site of the 5'-primer along the NOCIVA polynucleotide may be designed more freely. Thus, the 5'-primer can be designed to hybridize with a nucleic acid sequence shared at least in part by NOCIVA and CIP2A, i.e. the nucleic acid sequence encompassed by nucleotides 1-1634 of SEQ ID NO: 1. Alternatively, also the 5'-primer may be NOCIVA-specific, i.e. designed to anneal or hybridize specifically with a part of the intronic region formed by nucleotides 1635-1983 of SEQ ID NO: 1, a part of the NOCIVA peptide encoding sequence formed by nucleotides 1636-1674 of SEQ ID NO: 1, a part of the 3'UTR region of NOCIVA formed by nucleotides 1675-1983 of SEQ ID NO: 1, or the region overlapping the peptide-encoding region and the 3'UTR of NOCIVA.

In more general terms, the invention provides a primer pair for specific amplification of NOCIVA, wherein at least the 3'-primer is NOCIVA-specific, i.e. hybridizes with a subsequence of SEQ ID NO: 1 corresponding wholly or partly to the full-length intronic region, the peptide-encoding intronic region, or the 3-UTR intronic region (nucleotides 1635-1983, 1636-1674, or 1675-1983 of SEQ ID NO: 1, respectively). In some embodiments, both the 5'-primer and the 3'-primer are NOCIVA-specific. In some other embodiments, the 5'-primer comprises a sequence that anneals or hybridizes specifically with least a part of the a sequence shared by NOCIVA and CIP2A, i.e. a sequence formed by nucleotides 1-1634 of SEQ ID NO: 1. Typically, the primers are designed such that the length of the amplicon is from about 50 nucleotides to about 350 nucleotides when designed to only target the intronic NOCIVA sequence, i.e., nucleotides 1635-1983 of SEQ ID NO: 1. In the other words, when used in a nucleic acid amplification assay, the primers produce an amplification product with a length varying from about 50 to about 350 nucleotides.

Accordingly, in some embodiments the primer pair of the invention amplifies NOCIVA-specific intronic sequence only, i.e., at least part of the sequence defined by nucleotides 1635-1983 of SEQ ID NO: 1. In such embodiments, the 3'-primer of the primer pair hybridizes specifically with 10-40, preferably 15-35, more preferably 20-30 consecutive nucleotides of a sequence formed by nucleotides 1635-1983, 1635-1674, or 1675-1983 of SEQ ID NO:1 and the 5'-primer hybridizes specifically with 10-40, preferably 15-35, more preferably 20-30 consecutive nucleotides of a sequence formed by nucleotides 1635-1983, 1635-1674, or 1675-1983 of SEQ ID NO: 1.

In some other embodiments, the primer pair of the invention only amplifies a part of the NOCIVA-specific sequence defined by nucleotides 1635-1983 of SEQ ID NO: 1 so that the amplicon spans one or more nucleotides into the sequence shared by NOCIVA and CIP2A, i.e. the sequence formed by nucleotides 1-1634 of SEQ ID NO: 1. In such embodiments, at least the 3'-primer of the primer pair hybridizes specifically with 10-40, preferably 15-35, more preferably 20-30 consecutive nucleotides of a sequence formed by nucleotides 1635-1983, 1635-1674, or 1675-1983 of SEQ ID NO: 1. In further embodiments, the 5'-primer hybridizes specifically with 10-40, preferably 15-35, more preferably 20-30 consecutive nucleotides of a sequence formed by nucleotides 1-1984, 1-1635, 1635-1983, 1635-1674, or 1675-1983 of SEQ ID NO: 1. In many of such embodiments, the length of the amplicon produced by the 5'- and 3'-primers varies from about 50 to about 2000, preferably from about 60 to about 1000, more preferably from about 70 to about 500, and even more preferably from about 75 to about 250 nucleotides. Some non-limiting examples of suitable 5'- and 3'-primers are set forth in Table 2 and include 5'-primers selected from the group consisting of sequences set forth in SEQ ID NOs: 5-25, and/or 3'-primers selected from the group consisting of sequences set forth in SEQ ID NOs: 45-65. A person skilled in the art is well capable of designing primers according to any of the outlined embodiments, taking in account the space requirements for fitting both amplification primers and, optionally, probe(s) in the desired frame.

In many embodiments where a high amplification efficiency is pursued, the 5'- and 3'-primers of the primer pair have compatible melting temperatures (Tm), e.g., melting temperatures which differ by less than that 7° C., preferably less than 5° C., more preferably less than 4° C., most preferably less than 3° C., and ideally between 3° C. and 0° C.

Means and methods for considering any possible off-targeting when designing NOCIVA-specific oligonucleotides, such as primers and probes, and detection assays for NOCIVA are readily available in the art. It is sufficient if the oligonucleotide combination or assay to be used provide as a whole enough NOCIVA-specificity to enable reliable detection of NOCIVA expression.

Depending on the technique to be employed for detecting the amplification product, the primers may be detectable such that no probes are needed for the detection. Alternatively, intercalating labels (e.g. SYBR Green) can be employed. Combined with melting curve analysis, the intercalating labels can be used to detect and to differentiate between amplicons even with slight differences without the need for using probes. In an exemplary embodiment of the current invention, a 5'-primer common for both NOCIVA and CIP2A could be employed, combined with two 3'-primers, one of which specific for each sequence.

In accordance with the above, the expression of NOCIVA at nucleic acid level may be determined using any suitable method with or without nucleic acid amplification. For example, NOCIVA mRNA may be first converted into its complementary cDNA with the aid of a reverse transcriptase, followed by DNA amplification, e.g. by reverse transcriptase PCR (RT-PCR) including but not limited to quantitative PCR (qPCR), also known as real-time PCR. The presence, absence or concentration of the expressed NOVICA mRNA polynucleotide or an amplification product or a property thereof may be assessed according to methods available in the art, for example by using a NOCIVA-specific capture or detection probe. Further potential methods suitable for determining the expression of NOVICA at nucleic acid level, with or without a reverse transcription step and/or a nucleic acid amplification step depending on the method selected, include but are not limited to RNase protection assays, molecular beacon-based oligonucleotide hybridization assays, melting curve analysis combined with oligonucleotide probes and/or intercalating labels, gel electrophoresis analysis, Southern blotting, microarrays such as DNA microarrays and RNA microarrays, direct probing, and signal accumulation assays.

Accordingly, in some embodiments, the binding body is an oligonucleotide probe which can be utilized in various aspects of the present invention. Preferably, the probe is a single stranded polynucleotide which hybridizes specifically with a sequence or its complement corresponding wholly or partly to the unique sequence region of NOCIVA, i.e. the intronic region between exons 13 and 14 of KIAA1524 gene (corresponding to nucleic acids 1635-1984 of SEQ ID NO: 1). The present invention also encompasses probes that hybridize to sequences complementary to the sequences set forth above. In some embodiments, the probe may comprise or consist of a sequence that is not complementary to the whole said unique sequence region but only to a part thereof. In other words, an oligonucleotide probe of the present invention can be designed to hybridize with a nucleic acid sequence overlapping with or comprising at least a part of said intronic region.

The present NOCIVA-specific probes may vary in their length. Those skilled in the art can easily design a probe having a length that is suitable or optimal for the technique to be applied for determining the expression level of NOCIVA. For example, the target-specific part of the probe may have a length of 8-40, preferably 15-35, more preferably 20-30 nucleotides. In some embodiments the probe hybridizes specifically to NOCIVA but not to previously known CIP2A isoforms under moderate to stringent hybridization conditions, which conditions are apparent to those skilled in the art. Accordingly, such probes hybridize specifically to a region comprising or overlapping at least partly with the unique intronic region of NOCIVA, which intronic region is 350 nucleotides in length and corresponds to nucleotides 1635-1983 of SEQ ID NO: 1. Such probes are useful for example in embodiments where only the NOCIVA-specific sequence is to be detected irrespective of what expression or amplification products are present.

In some other embodiments, the probe hybridizes to or overlaps with the region preceding the NOCIVA-specific sequence, i.e., in the region which is at least in part present also in the known CIP2A isoforms, corresponds to nucleotides 1-1634 of SEQ ID NO: 1. Such probe is useful for example in embodiments where a previously known CIP2A isoform and NOCIVA are amplified in separate reaction wells and, e.g. for quantifying reasons, preferably detected with the same or essentially similar probe. Such probes are also useful e.g. in embodiments where the target sequence for the probe is present, i.e. for example amplification products are available for analysis only if the sample analyzed has contained NOCIVA-polynucleotides.

In yet further embodiments, at least two probes are employed, one specifically hybridizing to or overlapping with the intronic NOCIVA region corresponding to nucleotides 1635-1983 of SEQ ID NO: 1 and the other specifically hybridizing to or overlapping with the region common amongst all the CIP2A isoforms corresponding to nucleotides 1-1634 of SEQ ID NO: 1. Such probes are useful for example in embodiments where the amplification and detection of different CIP2A isoforms are performed in a multiplexed reaction. In such assays, additional or alternative probes can also be designed in the regions covering, for example, exons 1-13, 14-19 and/or 20-21.

Some non-limiting examples of suitable probes are set forth in Table 2.

If the present NOCIVA-specific probes are to be used in a method that involves use of the present primer pairs, it may in some embodiments be advantageous to design the probe such that its melting temperature is compatible with that of the primer pair to be used.

The NOCIVA-specific oligonucleotides, i.e. primers and/or probes of the present invention include, for example, those containing modified backbones, non-natural internucleoside linkages, and/or one or more base modifications or substitutions as is apparent to those skilled in the art. Moreover, the chemical composition of the probes may be e.g. DNA, RNA, locked nucleic acid (LNA), or peptide nucleic acid (PNA), or they may be composed of mixed polymers containing any number of monomers of DNA, RNA, LNA, PNA, or other nucleic acid analogues. Furthermore, the probes may be constructed as minor groove binding (MGB) probes.

In accordance with the above, the present invention provides a method determining the expression level of NOCIVA at nucleic acid level. Such a method may comprise, for example, contacting a sample from subject in need of said determination and suspected of containing NOCIVA mRNA or an isolated NOCIVA mRNA obtained from said sample with a oligonucleotide binding body, such as a probe, specifically interacting with NOCIVA mRNA or NOCIVA-specific nucleic acid assay amplification product under conditions wherein the binding body specifically hybridizes with said intended target; and detecting a hybridization complex, if any; wherein the presence of said hybridization complex correlates with the presence of NOCIVA mRNA in said sample.

The detection of hybridization complexes can be carried out by any suitable method available in the art. Hybridization complexes may in some assay methods be physically separated from unhybridized nucleic acids (e.g. by employing one or more wash steps to wash away excess target mRNA/cDNA, the probe, or both), and detectable labels bound to the complexes are then detected. More often, however, homogeneous detection is employed where no physical separation of hybridized and unhybridized molecules is required. In nucleic acid amplification assays, homogeneous detection may be performed as a separate step after amplification, i.e. using homogeneous end-point detection. The accumulation of the amplicon can also be homogeneously monitored during the amplification assay by use of qPCR type of methods. The various homogeneous detection methods can further be classified into probe-using and non-probe-using formats.

Detectable labels refer to radioactive, fluorescent, biological or enzymatic tags or labels of standard use in the art. A detectable label can be conjugated to either the oligonucleotide probe or the target polynucleotide. As is evident to those skilled in the art, the choice of a particular detectable label dictates the manner in which it is bound to the probe or the target sequence, as well as the technique to be used for detection. Although the present invention is not specifically dependent on the use of a label for the detection of a particular nucleic acid sequence, such a label might be beneficial, by increasing the sensitivity or specificity of the detection and simplifying the multiplexing of the assays. Furthermore, a detectable label may better enable automation.

Intercalating dyes (e.g. SYBR Green) can be used to detect the amplification of the DNA fragment of interest during a nucleic acid amplification reaction such as PCR. Intercalation occurs when ligands of an appropriate size and chemical nature position between the planar base pairs of DNA. These ligands are mostly polycyclic, aromatic, and planar, and therefore often make suitable nucleic acid stains. The intensity of fluorescence increases respectively during the amplification and it can be measured in real-time without the need of separate oligonucleotide probes.

As appreciated by those skilled in the art, a variety of controls and additives may be employed to improve accuracy of hybridization assays. For instance, samples may be hybridized to an irrelevant probe and/or treated with RNAse A prior to hybridization, to assess false hybridization or prevent unspecific or unwanted effects.

In some embodiments, the above-described detection method may comprise detecting the expression level of CIP2A by using CIP2A-specific primers and/or probes, which are readily available or can be designed using means and methods available in the art. The expression level of NOCIVA may be compared with that of CIP2A, wherein increased expression of NOCIVA is indicative of poor prognosis.

In some embodiments, determining the expression of NOCIVA is performed by sequencing techniques. Numerous methods suitable for this purpose have been described in the art and include, but are not limited to, traditional Sanger sequencing and next-generation sequencing (NGS) techniques. The present embodiments are not limited to any branded technique.

A representative commercial platform suitable for use in accordance with some embodiments of the invention, wherein the presence or quantity of NOCIVA, if any, is detected by sequencing, is Illumina's sequencing by synthesis (SBS) technology, particularly TruSeq® technology. Applying TruSeq® technology requires that two oligonucleotide probes, which hybridize upstream and downstream of the region of interest, are designed and synthetized. Each probe contains a unique, target specific sequence and a universal adapter sequence. An extension-ligation reaction is used to unite the two probes and create a library of new template molecules with common ends. Adapter-ligated DNA is then subjected to PCR amplification, which adds indexes and sequencing primers to both ends. Sequencing may then be performed by any suitable equipment, such as MiSeq® sequencer, utilizing a reversible terminator-based method enabling detection of single bases as they are incorporated into growing DNA strands.

Non-limiting examples of suitable equipment for the present sequencing purposes include Illumina® Sequencers, such as MiSeq™, NExtSeg500™, and HiSeq™ (e.g. HiSeq™ 2000 and HiSeq™ 3000), and Life Technologies' Sequencers, such as Ion Torrent™ Sequencer and Ion Proton™ Sequencer. It should be understood that utilizing any of these equipment requires that appropriate sequencing technique and chemistry be used.

In some embodiments relating to NGS techniques, detection of NOCIVA variant mRNA is possible with deep sequencing such as a one performed with Illumina HiSeq™ 3000 platform, 150 bp reading length and paired-end library.

In some embodiments of NGS-based techniques, the first probe to be employed hybridizes to a nucleic acid sequence encompassed by nucleotides 1-1634 of SEQ ID NO: 1, i.e. to a region corresponding to exons 1 to 13 of KIAA1524 and shared by NOCIVA and CIP2A, while the second probe to be employed hybridizes to a nucleic acid sequence that is specific for NOCIVA, i.e. either the unique intronic region or the 3'UTR described in more detail elsewhere in this application.

Further methods suitable for detecting the expression level of NOCIVA include, but are not limited to, RNA in situ hybridization technologies such as RNAscope® (Advanced Cell Diagnostics, ACD) and ViewRNAT™ (Invitrogen).

In accordance with the above, the present invention provides a method for any purpose set forth above, including but not limited to prognosing, detecting, screening, diagnosing, or monitoring cancer in a subject in need thereof, wherein the method comprises contacting a sample obtained from said subject with a reagent that specifically binds to the present NOCIVA polypeptide or NOCIVA polynucleotide; and determining the expression level of said polypeptide or polynucleotide on the basis of the binding of said reagent; and comparing the determined expression level to a relevant control; wherein increased expression of said polypeptide or polynucleotide is indicative of poor prognosis. Typically, said reagent is a NOCIVA-specific binding body according to the present invention, such as an anti-NOCIVA antibody or at least one NOCIVA-specific oligonucleotide, such as a probe and/or a primer pair.

In a further aspect, the present invention provides a kit for detecting the expression level of NOCIVA in a biological or clinical sample, for any purpose set forth above. Preferably, the kit comprises a NOCIVA-specific binding body, such as an anti-NOCIVA antibody or at least one NOCIVA-specific oligonucleotide, such a probe and/or a primer pair. In some embodiments, the binding body may comprise a detectable label. A person skilled in the art can easily determine any further reagents to be included in the kit depending on the desired technique for carrying out determination of the expression level of NOCIVA. Thus, the kit may further comprise at least one reagent for performing for example an immunoassay such as ELISA, a Western blot, immunohistochemical assay, nucleic acid amplification assay, signal amplification assay, in situ RNA hybridization assay, mass spectrometric assay or sequencing assay.

In some embodiments, an appropriate control reagent or sample or a threshold value may be comprised in the kit. The kit may also comprise a computer readable medium, comprising computer-executable instructions for performing any of the methods of the present disclosure.

It will be obvious to a person skilled in the art that, as technology advances, the inventive concept can be implemented in various ways. The invention and its embodiments are not limited to the examples described below but may vary within the scope of the claims.

EXPERIMENTAL PART

Material and Methods
3' RACE and 5' RACE

Extracted total RNA with Macherey-Nagel NucleoSpin RNA II-kit was used as a template for RACE experiments. For both 3' and 5' end cDNA amplification, Invitrogen 3'RACE (catalog no. 183743-019) and 5'RACE (catalog no. 18374-058) kits were used according to manufactures protocols. Multiple gene specific primers (GSPs) were designed and used for proper CIP2A related amplification of cDNA ends. Amplified sequences were run on agarose gels (percentage linked to the predicted fragment sizes), cut, DNA extracted (NucleoSpin® Gel and PCR Clean-up, Macherey-Nagel) and DNA sequenced for analysis. Sequencing primers were designed to be downstream of the GSPs.

RNA Isolation and cDNA Synthesis

Total RNA was isolated from cell line or extracted mononuclear cell (patient bone marrow samples) cell pellets. Total RNA from cell lines was extracted with NucleoSpin RNA II kit (Macherey-Nagel) and from patient samples the total RNA from mononuclear cells was isolated using the E.Z.N.A.® Total RNA Kit I (OMEGA bio-tek) according to the manufacturer's instructions. After isolation, RNA concentration was measured using a NanoDrop device (ND-1000; NanoDrop Technologies).

cDNA synthesis for all samples was performed using 1 μg of total RNA as a starting material. cDNA of cell lines was synthesized using M-MLV reverse transcriptase, Rnase (H-) (M3682, Promega), random primers (C1181, Promega), RNasin Ribonuclease Inhibitor (N2511, Promega) and dNTP mix (10 mM each, #R0192, Thermo Scientific). cDNA of patient samples was synthesized using SuperScript III Reverse Transcriptase (Ser. No. 18/080,093, Invitrogen), random primers (C1181, Promega), RiboLock™ Ribonuclease Inhibitor (#EO0381, Thermo scientific) and dNTP-mix (100 mM, BIO-39028, Bioline). RT-reactions, including temperatures and volumes, were performed according to enzyme's manufacturer's instructions.

Quantitative Real-Time PCR

Primers for each gene specific assay, if possible, were designed to be located to different exonic sequences to avoid amplification of genomic DNA. Primer concentration in each reaction was 300 nM and probe concentration 200 nM. Specificity of qPCR reactions was verified by agarose gel electrophoresis and melting curve analysis. One band of the expected size and a single peak, respectively, were required. Amplification of target cDNAs was performed using KAPA PROBE FAST qPCR Kit (Kapa Biosystems) and 7900 HT Fast Real-Time PCR System (Thermo Fisher) according to the manufacturers' instructions. Quantitative real-time PCR was executed under the following conditions: 95° C. for 10 min followed by 45 cycles of 95° C. for 15 s and 60° C. for 1 min. Relative gene expression data was normalized to expression level of endogenous housekeeping genes Glyceraldehyde-3-phosphate dehydrogenase (GAPDH) and beta acting using $2^{\wedge}\text{-}\Delta\Delta C(t)$ method with SDS software (version 2.4.1, Applied Biosystems). Results were derived from the average of at least two independent experiments and two technical replicates.

Primer and probe sequences for CIP2A e13 assay were: forward cagtctggactgagaatattgga (SEQ ID NO: 23), reverse ggcattgtttgctgctatactttt (SEQ ID NO: 66), probe tccactgc (SEQ ID NO: 42). Primer and probe sequences for CIP2A e20 assay were: forward gaacagataagaaaagagttgag-catt (SEQ ID NO: 67), reverse cgaccttctaattgtgcctttt (SEQ ID NO: 68), probe cttcctcc (SEQ ID NO: 69). Primer and probe sequences for b-actin assay were: forward tcacc-cacacrgtgcccatctacgc (SEQ ID NO: 70), reverse cagcg-gaaccgctcattgccaatgg (SEQ ID NO: 71), probe atgccctcccc-catgccatcctgcgt (SEQ ID NO: 72). Primer and probe sequences for GAPDH assay were: forward acccactcctc-cacctttga (SEQ ID NO: 73), reverse ttgctgtagccaaattcgttgt (SEQ ID NO: 74), probe acgaccact-ttgtcaagctcatttcctggt (SEQ ID NO: 75). Primer and probe sequences for EVI1 assay were: forward AGTGCCCTGGAGATGAGTTG (SEQ ID NO: 76), reverse TTTGAGGCTATCTGT-GAAGTGC (SEQ ID NO: 77), probe CCCCAGT-GAGGTATAA-AGAGGA (SEQ ID NO: 78). Primer and probe sequences for WT1 assay were: forward GGGCGTGTGACCGTAGCT (SEQ ID NO: 79), reverse CGCTATTCGCAATCA-GGGTTA (SEQ ID NO: 80), probe AGCACGGTCACCTTCGACGGG (SEQ ID NO: 81). Primer and probe sequences for PME1 assay were: forward acaggtttgcagaacccatc (SEQ ID NO: 82), reverse ggacagcaggtcactaacagc (SEQ ID NO: 83), probe tccagtgt (SEQ ID NO: 84). Primer and probe sequences for ARPP19 assay were: forward cagagggagcactatgtctgc (SEQ ID NO: 85), reverse gcttttaattttgcttcttctgct (SEQ ID NO: 86), probe universal probe library (UPL) #68. Primer and probe sequences for TIPRL assay were: forward catgatgatc-cacggcttc (SEQ ID NO: 87), reverse tcagggagagatggcatatgta (SEQ ID NO: 88), probe UPL #81. SET assay used was: SET5-6-3, AIY9AXG, Applied Biosystems.

Protein Expression and Purification

The truncated domains of human CIP2A (1-560, 1-330, 561-905) and full length NOCIVA were cloned into the pGEX-4T1 vector (GE Healthcare) with an N-terminal GST tag and a TEV cleavage site in between. All the constructs were overexpressed in *E. coli* BL21 (DE3) cells (Novagen), grown in LB media. The bacteria cells were cultured at 37° C. until OD600 reached 0.5-0.7, and then induced by 0.2 mM isopropyl β-D-1-thiogalactopyranoside (IPTG) at 16° C. overnight. The bacteria pellets were collected and lysed by sonication. The GST fusion proteins were purified by Glutathione Sepharose 4B column (GE17-0756-01, GE Healtcare). The purity of the samples was verified using SDS-PAGE and staining with Coomassie Brilliant Blue.

Antibodies

The following antibodies were used: mouse monoclonal anti-CIP2A (sc-80659, Santa Cruz); mouse monoclonal anti-nucleolin C23 (sc-17826, Santa Cruz), 4'6-diamidino-2-phenylindole (DAPI, Life Technologies), ECL HRP-linked secondary antibodies (GE Healthcare), Alexa Fluor-conjugated secondary antibodies (488 anti-rabbit, 594 anti-mouse, Life Technologies).

Western Blot

Protein extracts were separated using SDS-PAGE under denaturing conditions (4-20% Mini-PROTEAN TGX Gels) and were transferred to the PVDF membrane (Bio-Rad Laboratories). Membranes were blocked with 5% milk-TBST (Tris-buffered saline and 0.1% Tween 20), incubated with the indicated primary antibodies overnight at 4° C., and then incubated ECL HRP-linked secondary antibodies (GE Healthcare) at RT for 1 h. ECL Plus Western blotting reagent (GE Healthcare) was added to the membrane and film was developed.

Immunostaining

Cells were fixed with 4% PFA for 5 min at room temperature, washed, permeabilized with 0.2% Triton X-100+ 30% horse serum in PBS for 15 min and blocked with 30% horse serum in PBS for 30 min at room temperature. Cells were washed and then stained with the indicated primary antibodies diluted in 30% horse serum in PBS (1:100)

overnight at 4° C. Cells were then washed and incubated with Alexa-conjugated secondary antibodies (1:200) and 4'6-diamidino-2-phenylindole (DAPI, nuclei staining, 1:10, 000) 30% horse serum in PBS for one hour at room temperature. Optical fields of cells were imaged with Zeiss Zeiss AxioVert 200M (Carl Zeiss) inverted fluorescence microscope.

Immunohistochemistry

Tissue material was prepared according to standard histology practice, i.e. fixed in buffered formalin (pH 7.0) and embedded into paraffin blocks. Immunohistochemistry (IHC) was performed on sections cut at 3 µm. For antigen retrieval tissue sections were treated twice for 7 min each in citrate buffer in a microwave oven (Dako REAL Target Retrieval Solution, S2031, Dako, Glostrup, Denmark). IHC was carried out using a Lab Vision Autostainer 480 (Thermo-Fisher Scientific, Fremont, Calif., USA) and the signals were detected applying a PowerVision+ polymer kit, according to the manufacturer's protocol (DPVB+110HRP; Immunovision Technologies, Vision Biosystems, Norwell, Mass., USA), with diaminobenzidine as chromogen. NOCIVA specific antibodies (two separate, rabbit polyclonal, Biogenes) were applied at a dilution of 1:2000.

Statistical Analysis

Statistical analysis and comparisons were performed using JMP Pro 12 program. Continuous variables were summarised by descriptive statistics (median, interquartile range and range) while frequencies and percentages were calculated for categorical data. For continuous variables, the Mann-Whitney U-test was used for comparisons between independent samples and the Wilcoxon rank sum test was used for paired data. Overall survival functions were estimated by the Kaplan-Meier estimator and the log-rank test was used for comparisons between groups. Multivariate analysis was performed to study the relation of gene expression levels (under or over median) and response (death vs. alive for OS and relapse vs. non-relapse for relapse). All tests were two sided at a 5% significance level.

Identification of a Novel CIP2A Splicing Variant NOCIVA

Figure 1C:
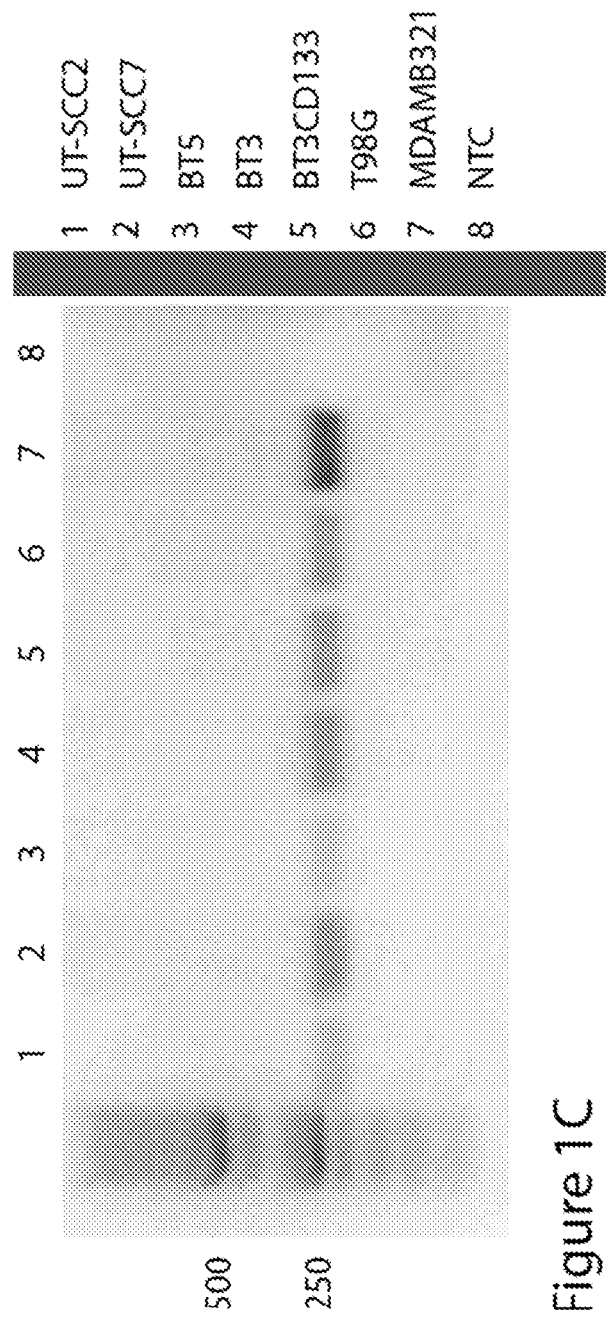
Figure 1D:
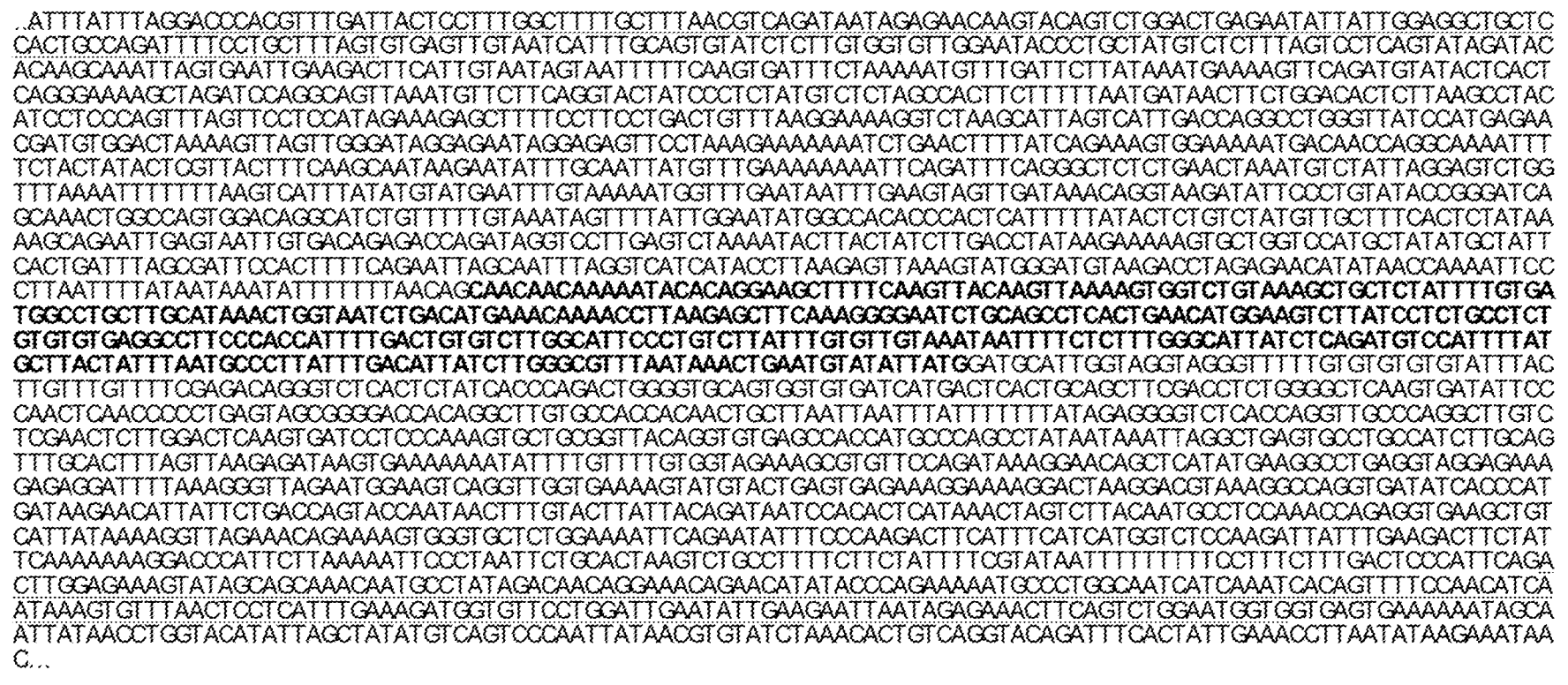

To identify potential mRNA variants of CIP2A, rapid amplification of cDNA ends PCR assays (3'RACE and 5'RACE) were employed in human cell line mRNA samples. As a result, we identified three CIP2A mRNA variants that were further validated with RT-PCR and sequencing (FIG. 1A). One variant form contained only CIP2A exons 1-19, and the other found variant contained exons 1-21, but lacked 3'UTR. Novel mRNA sequence, named as NOCIVA, was identified and it comprised exons 1-13 of CIP2A fused C-terminally to part of the intron between exons 13 and 14. FIG. 1D illustrates NOCIVA mRNA formation from KIAA1524 gene though alternative splicing. Intronic region (bolded in FIG. 1D) in between the KIAA1524 gene exon13 and exon14 (underlined in FIG. 1D) is considered as an alternative exon by the splicing machinery and attached to the end of the exon13. After processing the pre-mRNA to mature mRNA, poly(A) tail is attached to NOCIVA transcripts 3' end. NOCIVA transcript thus formed an unique and previously unknown sequence (FIGS. 1A and B). Interestingly NOCIVA specific intronic sequence is in coding frame with preceding CIP2A mRNA sequence, and after 40 nucleotides, corresponding to 13 amino acids, is followed by classical stop codon TAA (FIG. 1B). Potential 3'UTR of NOCIVA consists of appr. 350 nucleotides followed by AATAAA sequence, and classical poly-A sequence. Thus NOCIVA gene product codes for truncated CIP2A with 13 new amino acids (SEQ ID No: 3;NNKNTQEAFQVTS) at the C-terminal end (FIG. 1B). Importantly, this 13 aa peptide sequence do not match with any known protein sequence in human proteome based on Blast homology search (Table 1). Validation PCR for NOCIVA expression was conducted in multiple cell lines with primers specific for mRNA coding for unique C-terminal portion of NOCIVA (FIG. 1C). The correct size bands from the gel were subsequently sequenced to confirm that the PCR product represented NOCIVA mRNA product.

TABLE 1

Sequences producing significant alignments with SIVA in BLAST search:

| | Max Score | E-value | Identity |
|---|---|---|---|
| NP_001001715.2 PERM, RhoGEF and pleckstrin domain-containing . . . | 23.5 | 17 | 75% |
| BAF83484.1 unnamed protein product [Homo sapiens] | 23.5 | 17 | 78% |
| NP_005757.1 PERM, RhoGEF and pleckstrin domain-containing pro . . . | 23.5 | 17 | 75% |
| NP_001273768.1 PERM, RhoGEF and pleckstrin domain-containing . . . | 23.5 | 17 | 75% |
| AAH71592.1 FARP1 protein [Homo sapiens] | 23.5 | 17 | 75% |
| EAW78561.1 hCG1786642, isoform CRA_a [Homo sapiens] | 22.7 | 35 | 75% |
| AAH64971.1 IQGAP1 protein [Homo sapiens] | 22.7 | 35 | 86% |
| BAG65182.1 unnamed protein product [Homo sapiens] | 22.7 | 35 | 86% |
| AAI39732.1 IQ motif containing GTPase activating protein 1 [H . . . | 22.7 | 35 | 86% |
| NP_003861.1 ras GTPase-activating-like protein IQGAP1 [Homo s . . . | 22.7 | 35 | 86% |

NOCIVA Expression in Cancer Cells

Figure 2A:
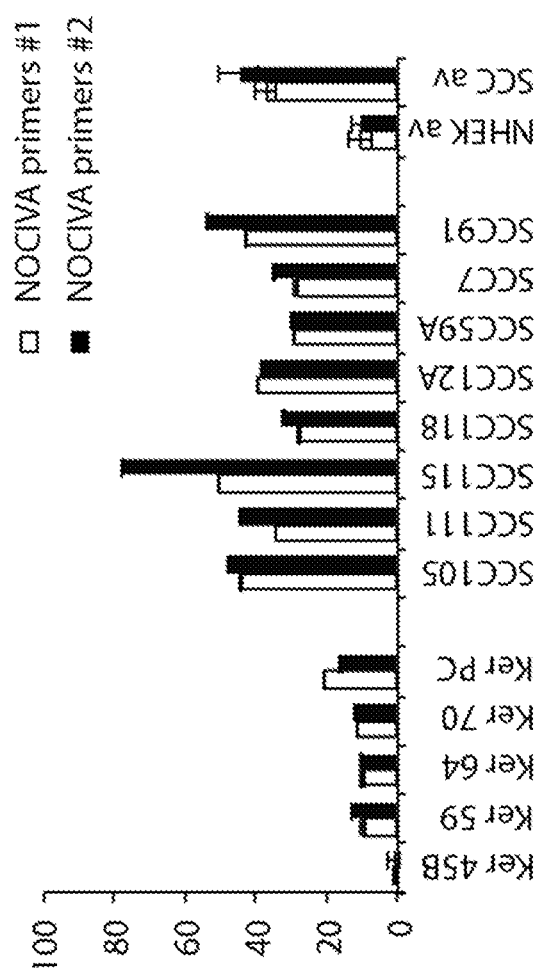
FIGS. 2A to 2E show NOCIVA and CIP2A mRNA expression in normal and cancerous cell and tissue samples.

To study the expression of NOCIVA mRNA variant in normal and cancerous tissues, we conducted qPCRs with two NOCIVA specific primer-probe-sets (primer and probe pairs 16 and 17 of Table 2) in panel of normal cells and cancerous cells. Patient-derived keratinocyte (Ker) samples were used as a model for normal tissue, and head- and neck squamous cell carcinoma (SCC) cell samples for cancerous tissue. Previously, CIP2A has been shown to be significantly overexpressed in HNSCC samples, and its high expression correlates with poor patient prognosis in human HNSCC (Ventela et al., 2015). Interestingly, NOCIVA expression also showed significantly elevated expression in SCC samples as compared to Ker (FIG. 2A).

Figure 2B:
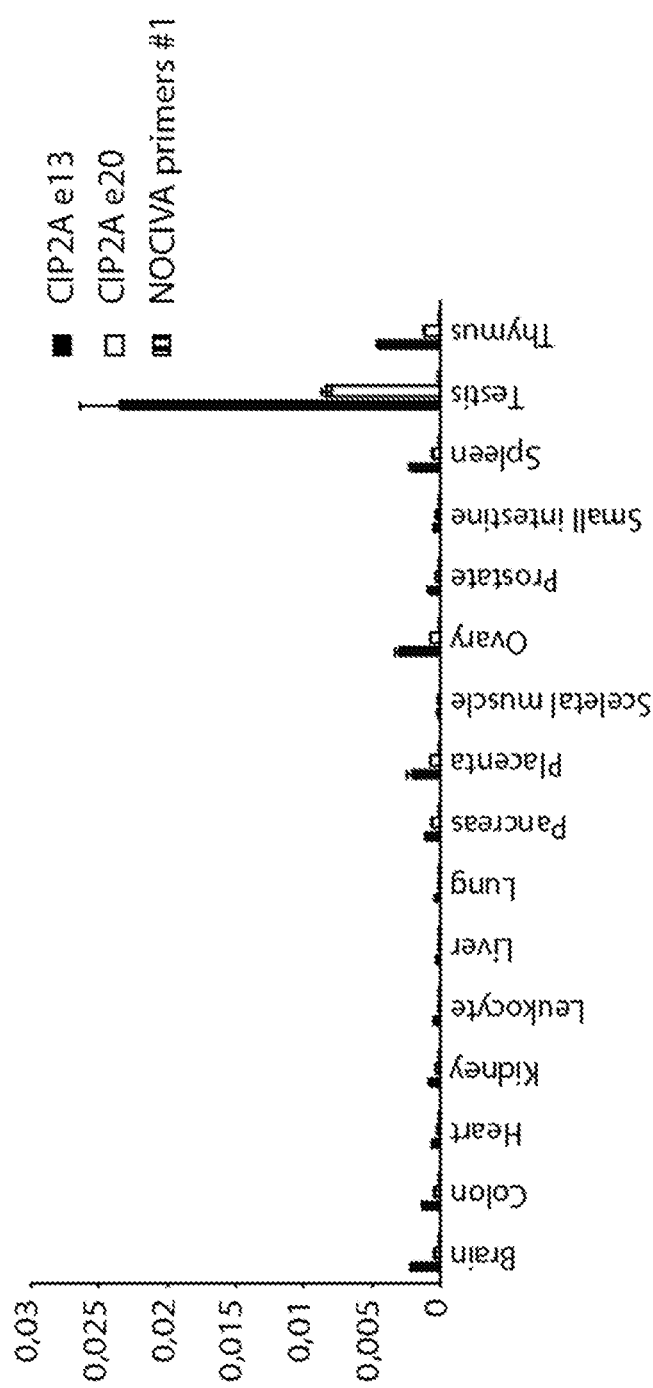

Next we assessed expression of CIP2A and NOCIVA in a panel of normal human tissue cDNAs (Human MTC panel I & II, Clontech, cat no 636742 & 636743). Notably, CIP2Ae13, CIP2Ae20 and NOCIVA PCR primers were optimized to yield similar amplification efficiency ruling out the possibility that potential differences in expression levels would be due to technical PCR assay-related reasons. Consistent with published evidence (Ventela et al., 2012), CIP2A was expressed at low levels in most of the normal human tissues, except for testis (FIG. 2B). Interestingly, CIP2A exon 13 primers (CIP2Ae13), which specifically amplify CIP2A but not NOCIVA, showed markedly higher expression levels than CIP2A exon 20 primers (CIP2Ae20). As compared to CIP2A, NOCIVA showed overall very low level of expression across normal human tissues (FIG. 2B).

Figure 2C:
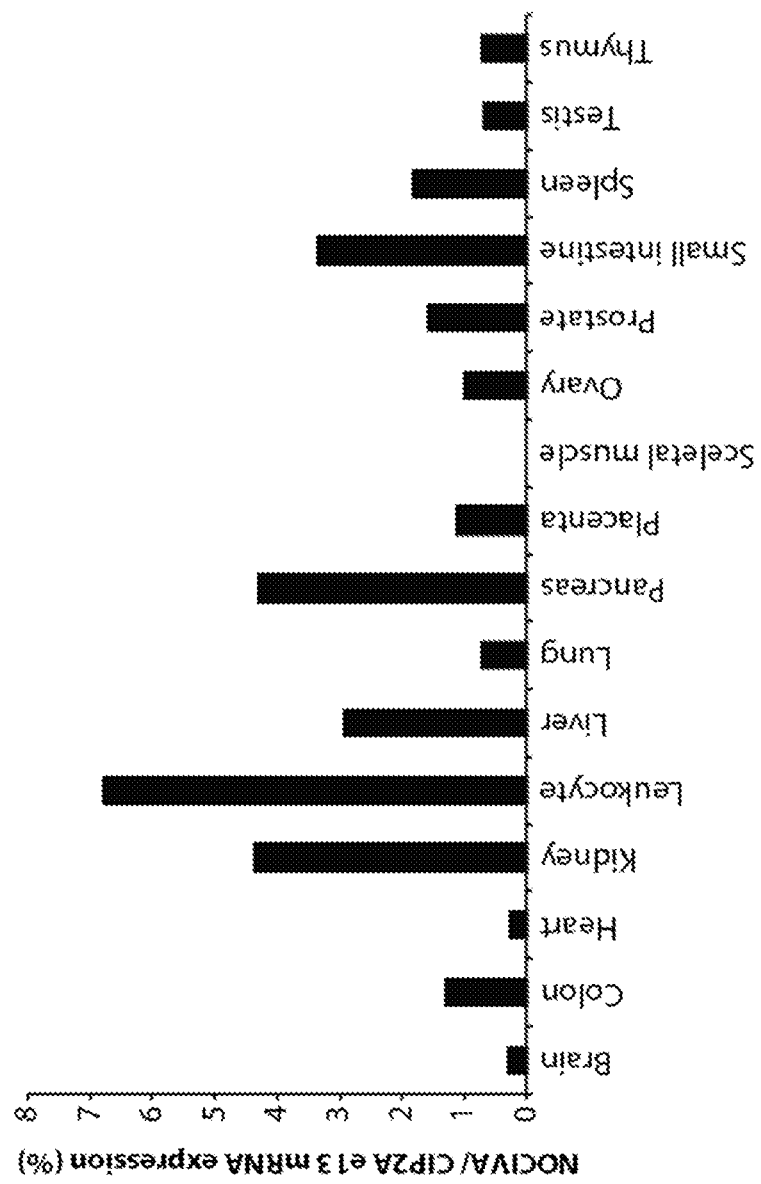
Figure 2D:
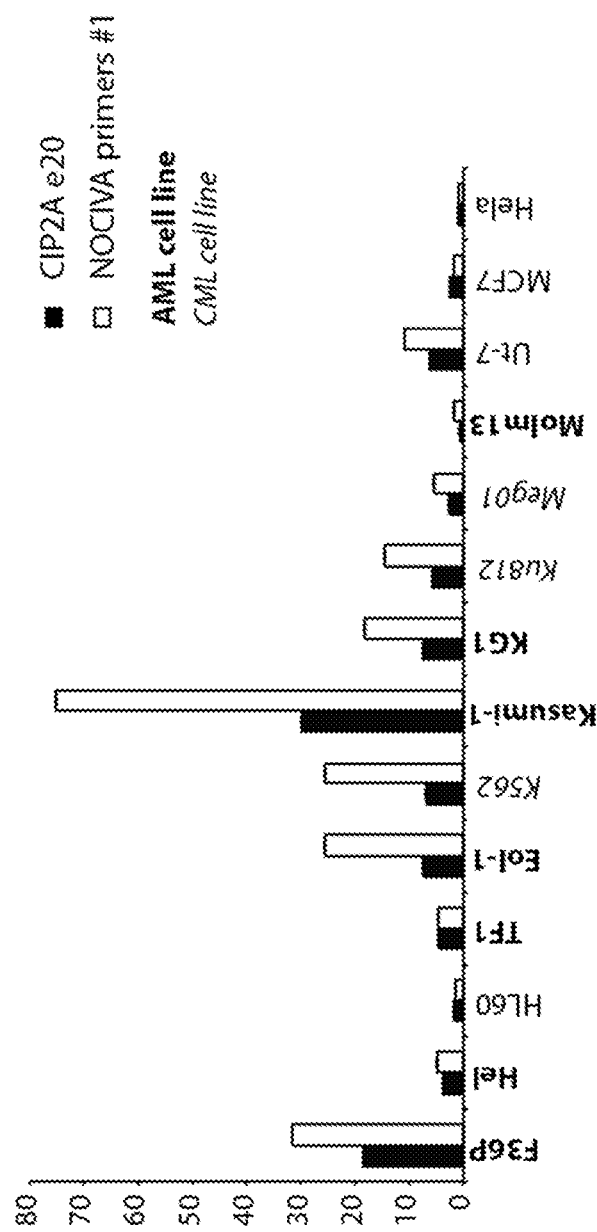
Figure 2E:
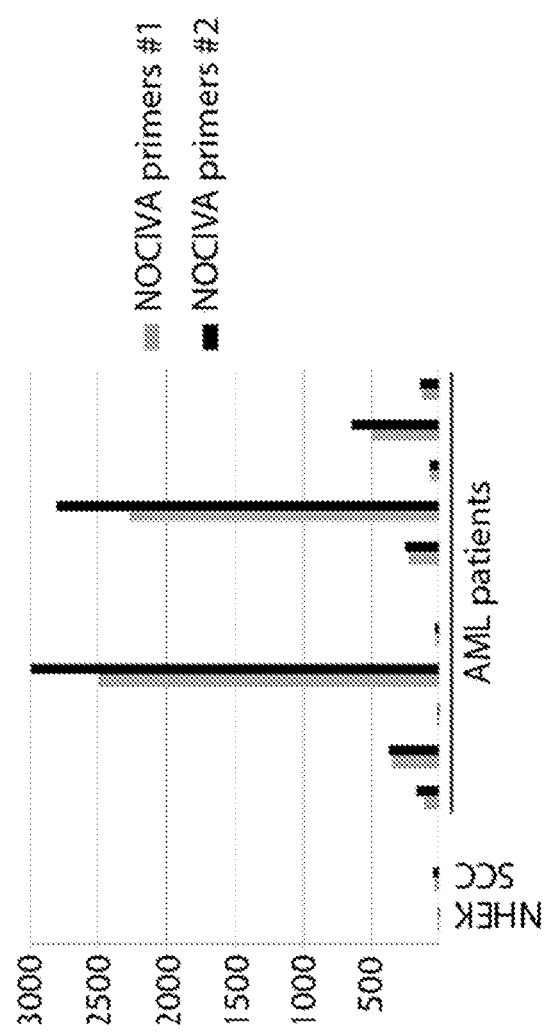

Although NOCIVA mRNA was expressed at very low level in all human normal tissues, the correlation of NOCIVA expression to CIP2A e13 expression facilitated analysis of those tissues in which NOCIVA expression was relatively most abundant to CIP2A. Out of the tissues analyzed, the leukocytes displayed highest NOCIVA/CIP2Ae13 ratio (FIG. 2C). Thus, in order to examine whether the already observed difference between normal and cancerous tissues (FIG. 2A) would be relevant to other cancer types, we next concentrated on lymphoid cancers acute myeloid leukemia (AML), chronic myeloid leukemia (CML) and acute promyelocytic leukemia (APL). Notably, as compared to cancer cell lines representing solid human cancers UT-7 (HNSCC), MCF-7 (breast cancer), and HeLa (cervical cancer), many AML cell lines, but also CML cell lines, showed clearly higher expression of NOCIVA mRNA (FIG. 2D). Even more interestingly, those AML and CML cell lines that expressed NOCIVA at higher level than in UT-7, showed also relatively higher expression of NOCIVA than CIP2Ae20 (FIG. 2D). In fact, higher expression of NOCIVA than CIP2Ae20 was also observed in UT-7 cells to some extent. These results reveal that lymphoid cancers, including AML and CML, consist of a cancer types in which NOCIVA expression is increased and could be clinically relevant. We thus postulate that upon oncogenic transformation there is a splicing switch that increases expression of NOCIVA coding alternative transcript as compared to full-length CIP2A. In order to validate overexpression of NOCIVA in AML, we analyzed a small cohort of AML diagnostic patient bone marrow samples and compared NOCIVA levels in those to average expression in either keratinocytes or HNSCC cells. Notably 6/8 of AML patient samples showed clearly higher expression of NOCIVA than in average levels found from HNSCC cells (FIG. 2E).

NOCIVA Overexpression in Human Lymphoid Diagnostic Samples

Figure 3A:
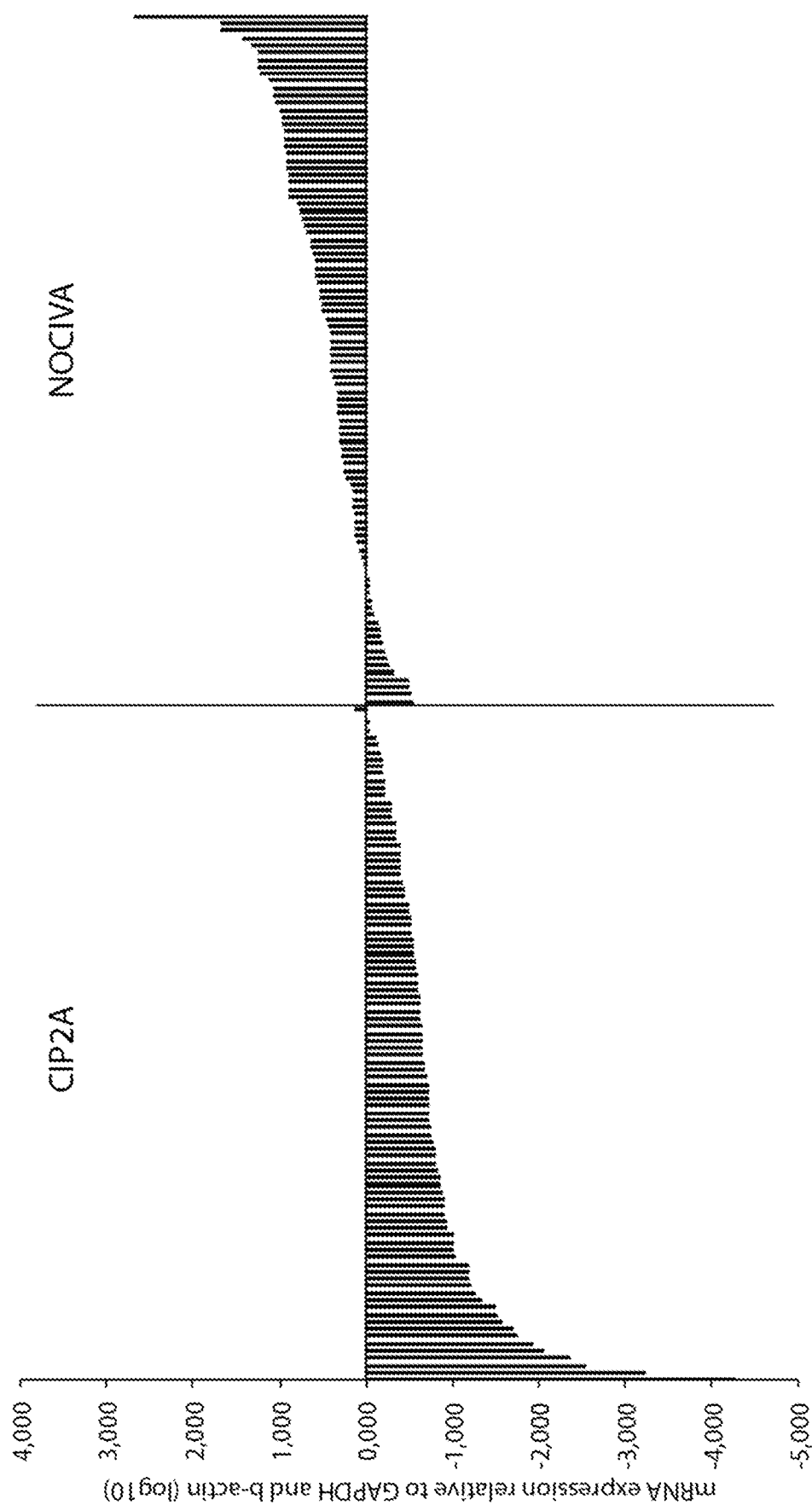

To further validate NOCIVA and CIP2A mRNA status in AML patient samples, we employed qPCR in larger sample panel of diagnostic AML patient bone marrow samples. The sample panel was collected between January 2000 and July 2010 and consist of total 93 patients aged 18-65 and diagnosed with de novo or secondary AML at Turku University Central Hospital (TYKS). Valid ethical permission have been obtained both for sample collection and for expression profiling described here. GAPDH and b-actin were used as housekeeping genes for expression normalization in each sample. To estimate degree of overexpression in AML, expression of both NOCIVA and CIP2A e20 in AML samples was normalized to levels of these genes in commercial normal bone marrow (BM) control sample (Clontech). In addition to CIP2A and NOCIVA, the samples were analyzed for expression of known AML markers WT1 and EVI1 and for other PP2A inhibitor proteins, SET that previously has been implicated in AML (Ciccone et al., 2015). Almost all patients expressed lower level of CIP2Ae13 or CIP2Ae20 as compared to normal bone marrow sample, whereas in total 78% of AML samples displayed overexpression of NOCIVA (FIGS. 3A and B). The percentage of patients showing NOCIVA overexpression greater than 2-fold over normal bone marrow sample was 68%. WT1, EVI1 and SET showed expression patterns that are in accordance to published literature.

Clinical Relevance of NOCIVA Expression in Human AML Diagnostic Samples

Figure 4E:
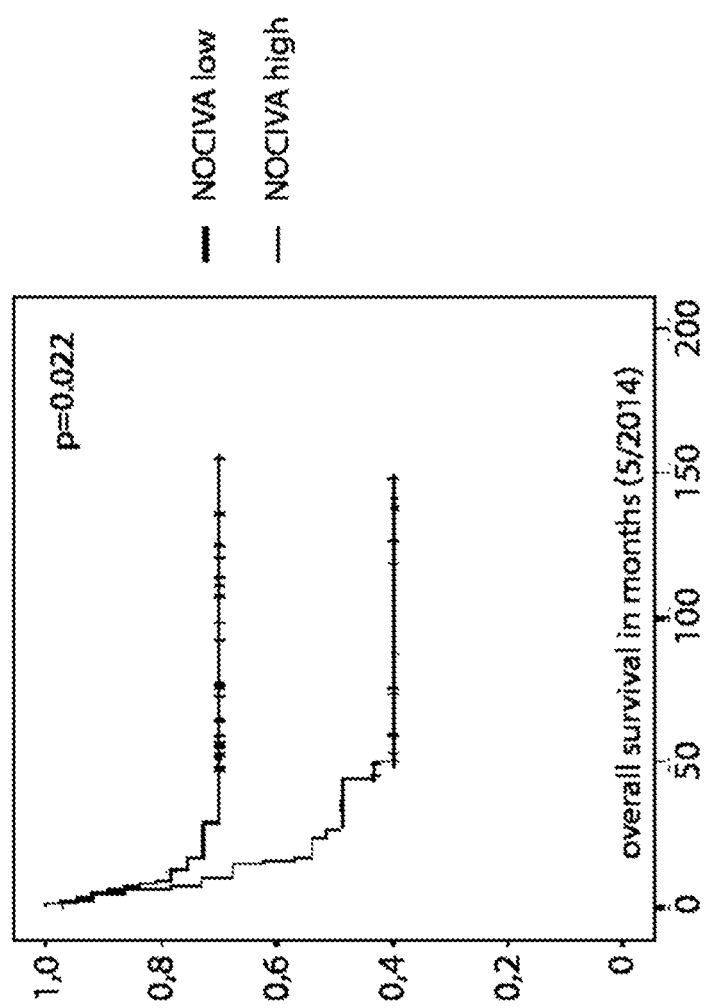

Of the 93 patients analyzed above, clinical follow-up information was available for 80 patients. Distribution of these patients to clinically used risk groups based on their genetic profiles is presented in FIG. 4A. In a multivariate analysis for overall survival (OS), diagnostic age, and both intermediate (risk group 2) and adverse (risk group 3) risk groups significantly correlated with poor patient survival (FIG. 4B). Next we assessed whether expression of NOCIVA, CIP2Ae13, CIP2Ae20, WT1, EVI1, or SET associates with risk groups. The only statistically significant association was found with EV1 expression when compared to difference between all risk groups (FIG. 4C). These data indicate that NOCIVA expression is independent of currently used AML risk group classification. Importantly, high NOCIVA expression did significantly correlate with poor OS in multivariate analysis with hazard ratio higher than for EVI1 expression (1.511 vs. 1.265)(FIG. 4D). Very interestingly, low CIP2Ae13 expression instead was a borderline significance predictor of better patient survival with hazard ratio of 0.173 (FIG. 4D). In Kaplan-Meier analysis of patient overall survival using NOCIVA mRNA expression levels divided to two groups, high and low, relative to median, NOCIVA high expressing patients also showed significantly poorer survival (FIG. 4E, p=0.022). Lastly, as high NOCIVA is associated with poor OS, whereas low CIP2Ae13 seems to rather associate with good OS, we tested whether high NOCIVA/CIP2Ae13 ratio could function as a novel diagnostic marker predicting for poor AML patient OS. As shown in FIG. 4F, this is the case as NOCIVA/CIP2Ae13 ratio showed statistically very significant association with poor OS in multivariant analysis.

Figure 6:
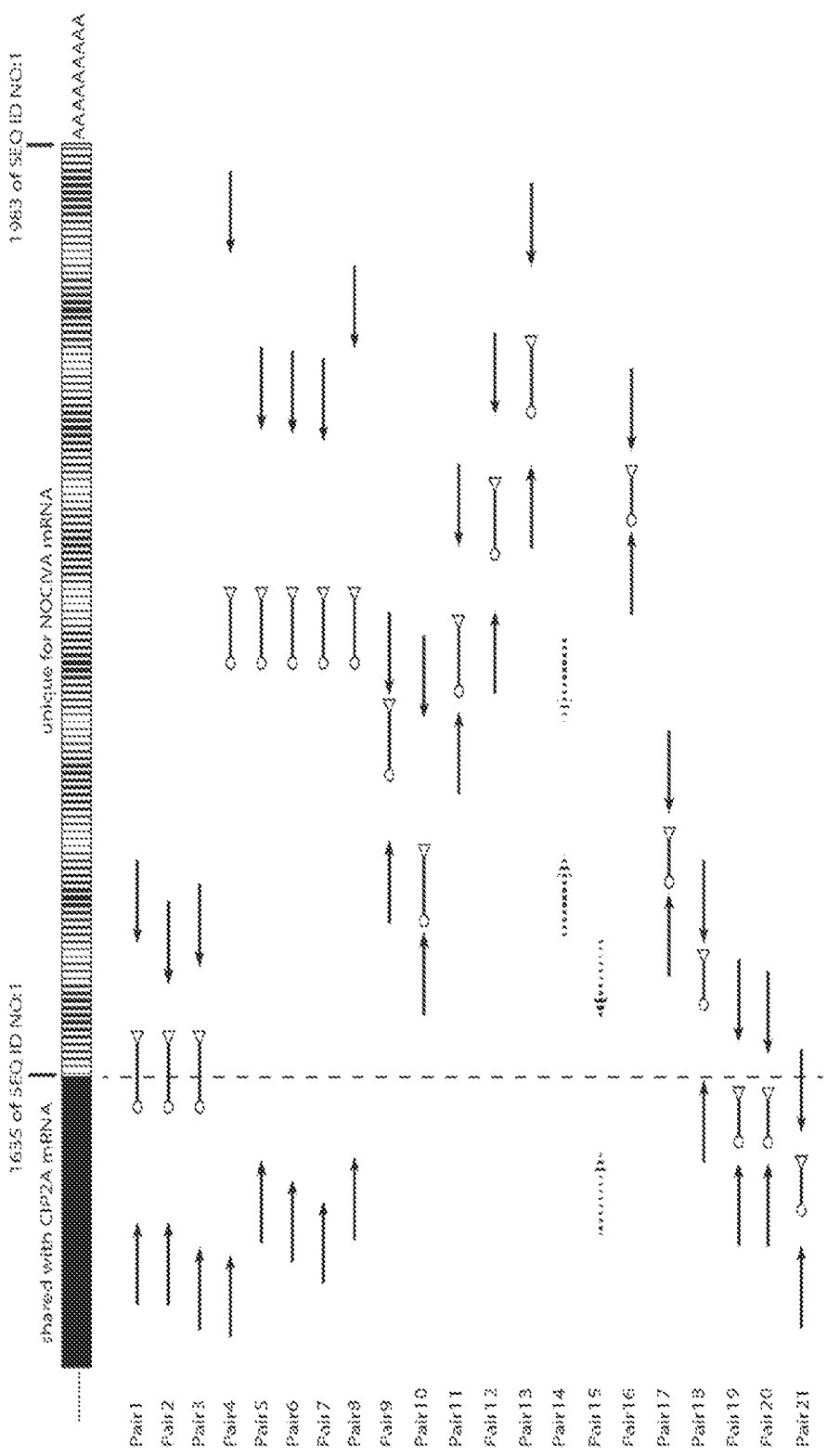
FIG. 6 illustrates a schematic presentation of non-limiting examples of oligo design for detection of NOCIVA specific sequence with PCR or qPCR. Dashed line marks the end of normal CIP2A mRNA sequence and the beginning of NOCIVA specific mRNA sequence. ◆━━━━━ primer, ┈┈┈┈┈ intercalated primer, ○━━━◁ probe.

Different sets of primer and probe sequences for the amplification and detection of NOCIVA-specific cDNA were designed according to general lines illustrated in FIG. 6 using Primer3Plus, IDT PrimerQuest Tool, and Roche Assay Design Center. The designs were either made manually with the help of Primer3Plus suggestions or they were recommended by the oligonucleotide design program used. Melting temperatures were calculated by the programs during assay designs. The assays were designed to be mainly used in qPCR setup, but also additional assays for traditional PCR were designed with Primer3Plus. Primers were typically designed to amplify 70 to 150 bp product. Typically primer length was set to be 18-23 bp, primer Tm 58-62° C., primer GC % 30-80 and maximum primer pair Tm difference 3° C. Probe length was typically set to be 18-27 bp, oligo Tm 60-68° C. and oligo GC % 20-80. When a minor groove binding (MGB) or locked nucleic acid (LNA) probe was were designed, Tm for the probe was calculated to be close to 60° C. so that the chemical modification would raise the probe Tm closer to 68-70° C. MGB assay design was done manually using Primer3Plus while LNA assay design was made automatically by Roche Design Centre. Roche Design Centre uses Roche's universal probe library in the designs. Details of the sequences, melting temperatures and probe chemistry for each assay design is provided in Table 2.

TABLE 2

Examples of designed primers and probes

| | 5'-primer sequence (SEQ ID NO:) | Tm | Probe sequence (SEQ ID NO:) | Tm | Probe chemistry | 3'-primer sequence (SEQ ID NO:) | Tm | Amplicon lenght (bp) | Design type* | SYBR validated | Design method** |
|---|---|---|---|---|---|---|---|---|---|---|---|
| Pair1 | 5 | 59.4 | 26 | 60.7 | MGB | 45 | 61.2 | 140 | M | No | 1 |
| Pair2 | 6 | 59.4 | 27 | 60.7 | MGB | 46 | 59.6 | 103 | M | No | 1 |
| Pair3 | 7 | 58.1 | 28 | 60.7 | MGB | 47 | 58.5 | 142 | M | No | 1 |
| Pair4 | 8 | 60.2 | 29 | 60.0 | None | 48 | 57.7 | 401 | R | No | 2 |
| Pair5 | 9 | 59.5 | 30 | 60.0 | None | 49 | 59.0 | 304 | R | No | 2 |
| Pair6 | 10 | 59.2 | 31 | 60.0 | None | 50 | 59.5 | 306 | R | No | 2 |
| Pair7 | 11 | 61.0 | 32 | 60.0 | None | 51 | 59.9 | 307 | R | No | 2 |
| Pair8 | 12 | 59.7 | 33 | 60.0 | None | 52 | 60.3 | 349 | R | No | 2 |
| Pair9 | 13 | 62.0 | 34 | 68.0 | None | 53 | 62.0 | 107 | R | No | 3 |
| Pair10 | 14 | 62.0 | 35 | 68.0 | None | 54 | 62.0 | 129 | R | No | 3 |
| Pair11 | 15 | 62.0 | 36 | 68.0 | None | 55 | 62.0 | 99 | R | No | 3 |
| Pair12 | 16 | 62.0 | 37 | 68.0 | None | 56 | 62.0 | 115 | R | No | 3 |
| Pair13 | 17 | 62.0 | 38 | 67.0 | None | 57 | 62.0 | 114 | R | No | 3 |
| Pair14 | 18 | 62.0 | | | NA | 58 | 62.0 | 102 | R | No | 3 |
| Pair15 | 19 | 62.0 | | | NA | 59 | 62.0 | 95 | R | No | 3 |
| Pair16 | 20 | 59.0 | 39 | 60.0 | LNA | 60 | 60.0 | 68 | R | Yes | 4 |
| Pair17 | 21 | 59.0 | 40 | 60.0 | LNA | 61 | 59.0 | 68 | R | Yes | 4 |
| Pair18 | 22 | 59.0 | 41 | 60.0 | LNA | 62 | 60.0 | 129 | R | No | 4 |
| Pair19 | 23 | 59.0 | 42 | 60.0 | LNA | 63 | 59.0 | 96 | R | Yes | 4 |
| Pair20 | 24 | 59.0 | 43 | 60.0 | LNA | 64 | 59.0 | 87 | R | Yes | 4 |
| Pair21 | 25 | 60.0 | 44 | 60.0 | LNA | 65 | 59.0 | 127 | R | Yes | 4 |

*M, manual design;
R, recommended design
**1, manually on the basis of Primer3Plus search
2, Primer3Plus
3, IDT PrimerQuest Tool
4, Roche Assay Design Center Development of CIP2A Exon 16 Assay and Re-Evaluation of Existing Results Based on NOCIVA/CIP2Ae16 Ratio CIP2A may be distinguished from NOCIVA on the basis of the presence of exon 16 (CIP2Ae16). To this end, an assay described below is developed. TaqMan® Gene Expression Assay for CIP2A exons 16, Hs00405413_m1, from Life Technologies already exists and this is also tested for the same sample material. Alternative or additionally, CIP2A may be distinguished from NOCIVA on the basis of CIP2Ae13 or CIP2Ae20 as is described in examples above.

Total RNA is isolated using the RNeasy minikit (Qiagen). cDNA is synthesized with SuperScriptIII Reverse Transcriptase (Invitrogen) according to manufacturer's instructions. Quantification of the expression of CIP2A e16 is performed using TaqMan Gene Expression Assay (Applied Biosystems). Glyceraldehyde 3-phosphate dehydrogenase and beta acting is used as internal control. KAPA PROBE FAST qPCR Kit is used for qPCR reaction and QuantStudio™ 12K Flex Real-Time PCR System for plate run. PCR reaction cycle: 1: 95° C. 10 min, 2: 95° C. 15 sec, 3: 60° C. 1 min; repeat steps 2-3×45. Analysis of relative gene expression data is performed using the 2-ΔΔCT method with Thermo Fisher Cloud software. A gene is considered deregulated if its expression value is higher or lower than the cutoff value established for each gene (mean+3 s.d.), defined by the analysis of normal BM control sample (Clontech, Human Bone Marrow total rna).

NOCIVA Taqman in Chronic Myelogenous Leukemia Cells and Other Hematological Malignanices Quantification of the expression of NOCIVA gene expression in other hematological malignancies and established cell lines, including cronic myeloid leukemia, is performed using TaqMan gene expression assays designed in Roche Design Centre. Assays are validated by melting curve and amplification efficiency analysis. Total RNA is isolated using the RNeasy minikit (Qiagen) from monoclonal cell extract. cDNA is synthesized with SuperScriptIII Reverse Transcriptase (Invitrogen) according to manufacturer's instructions. Glyceraldehyde 3-phosphate dehydrogenase and beta acting is used as internal control. KAPA PROBE FAST qPCR Kit is used for qPCR reaction and QuantStudio™ 12K Flex Real-Time PCR System for plate run. PCR reaction cycle: 1: 95° C. 10 min, 2: 95° C. 15 sec, 3: 60° C. 1 min; repeat steps 2-3×45. Analysis of relative gene expression data is performed using the 2-ΔΔCT method with Thermo Fisher Cloud software. A gene is considered deregulated if its expression value is higher or lower than the cutoff value established for each gene (mean+3 s.d.), defined by the analysis of normal BM control sample (Clontech, Human Bone Marrow total rna)

In Situ Techniques for Detecting NOCIVA in Solid Cancers

RNA in situ hybridization technologies including RNAscope® (Advanced Cell Diagnostics, ACD) and ViewRNA™ (Invitrogen) are tested for NOCIVA and CIP2A detection according to manufacturer's instructions in various formalin-fixed solid cancer cell lines and formalin-fixed, paraffin-embedded (FFPE) tissue samples (breast, prostate, HNSCC at least). Negative and positive biological controls are chosen based on prior qPCR analysis of the similar samples for CIP2A and NOCIVA detection. Technical controls are included to the experimental settings according to manufacturer's instructions. ACD and Invitrogen will be contacted for novel probe design for CIP2A and NOCIVA mRNA in situ detection. ACD and Invitrogen will design and manufacture the in situ hybridization probes for CIP2A and NOCIVA detection. Analysis of the received read-out will be examined according to manufacturer's instructions.

Generation of NOCIVA Specific Antibodies

Two NOCIVA specific antibodies were generated by immunizing rabbits against NOCIVA specific peptide NNKNTQEAFQVTS (SEQ ID NO: 3) by BioGenes GmbH. Upon peptide synthesis (purity at least 80%, quality control by HPLC and MS), an additional N-terminal cysteine was added to the NOCIVA-specific peptide for directed conjugation with a carrier protein.

Monospecific IgG antibodies were purified from post-immunization sera by affinity chromatography using a NOCIVA-peptide (SEQ ID NO: 3) antigen column with CNBr-activated Sepharose™ as the affinity matrix.

Figure 5:
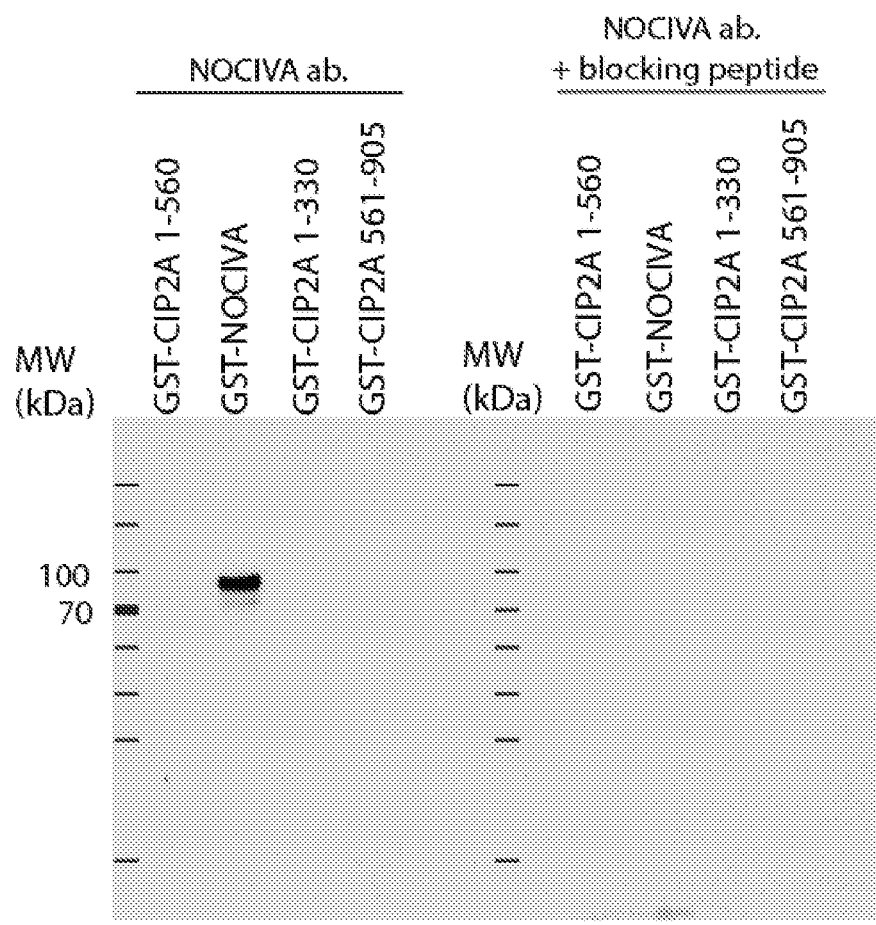
FIG. 5 shows that a NOCIVA specific antibody detects correct size (appr. 90 kDa) recombinant GST-NOCIVA protein, but not recombinant CIP2A fragments. Signal can be blocked with a NOCIVA-blocking peptide.

Specificity of the affinity-purified antibodies was tested with bacterially expressed recombinant proteins (FIG. 5), as well as with overexpressed GFP-NOCIVA fusion protein in cells. Blocking peptide, also composed of SEQ ID NO: 3, was used as control. Both antibodies detected both recombinant bacterially produced purified GST-NOCIVA (FIG. 5), as well as GFP-NOCIVA overexpressed in Hela cells (data not shown). Importantly, NOCIVA antibodies were specific, and they did not recognize any of the recombinant CIP2A fragments (FIG. 5).

Use of NOCIVA-Specific Antibodies for Diagnostic Immunohistochemistry in Solid Human Cancer Tissue Samples Applicability of the NOCIVA-specific antibodies generated as described above for diagnostic immunohistochemistry (IHC) was tested and optimized. It is important to choose an appropriate IHC method for a trustworthy detection result. Tissue microarray (TMA) consisting of paraffin embedded samples from head and neck squamous cell carcinoma and breast cancer tissues was stained with antibody generated against NOCIVA specific peptide.

The Labeled StreptAvidin Biotin (LSAB) technique does not have the sensitivity for some antigenic expression, where use of polymer systems or tyramine amplification may be required in its stead. The comparison of pH6 and pH9 heat induced epitope retrieval (HIER) buffers together with incubation of the antibody at two dilutions/concentrations provide an initial indication of which combination is worth pursuing further. Other variations that are tested include the temperature and time of HIER, range of antibody dilution/concentration and primary antibody incubation. Alternative fixatives can be investigated but can only be applied to minor group of samples, as the majority of tissue collections in both research and clinical arena's utilize neutral buffered formaldehyde. Care is also taken to approach variation of the technique systematically, to employ the same reagent batches throughout the validation and to record staining results using a standardized reporting template.

In addition to approaches routinely used for validation and optimization of a new antibody for diagnostic IHC use, NOCIVA-depleted cells are used as a specificity control in a cell lysate microarray (CMA) format recently developed in the inventors' laboratory. NOCIVA depleted cells serve as the negative biological control in this setup. Positive control is chosen based on prior western blot analysis of the similar tissue samples for NOCIVA detection. For research purposes, NOCIVA-specific antibodies are also tested and the performance thereof is validated in various tissue and cell lysate samples (including breast, prostate and HNSCC samples) to assess all the use indications (cancer types) in which NOCIVA functions as a biomarker.

Use of NOCIVA-Specific Antibodies for Diagnostic FACS Analysis Both in Hematological and Solid Cancers The NOCIVA-specific antibodies generated as described above are validated and optimized for use in diagnostic fluorescence-activated cell sorting (FACS). To this end, a protocol is developed to investigate the predictive value of measuring NOCIVA in freshly collected peripheral blood and bone marrow samples at the time of diagnosis. Sample preparation is done according to TYKSlab's protocol for handling hematological patient samples for FACS analysis. In a typical FACS protocol for hematological samples, cells are resuspended in 500 µl of 2% paraformaldehyde, fixed for 10 min at 37° C. and chilled on ice for 1 min. The cells are harvested by centrifugation (770 g, 3 min), 500 µl 90% methanol is added after which the samples are vortexed briefly and incubated on ice for 30 min. The cells are then washed (throughout with 1 ml of an incubation buffer containing phosphate-buffered saline and 0.5% bovine serum albumin), harvested and resuspended in 25 µl of the incubation buffer. After this the samples are incubated at room temperature for 10 min. The antibodies are added to a final concentration of 30 µg/ml, vortexed and incubated at room temperature for 40 min. The samples are washed twice, resuspended in fluorescein-labelled secondary antibody Alexa Fluor 488 (10 µg/ml), and incubated at room temperature in the dark for 30 min. Twice washed cells are then analysed using flow cytometry (FACScalibur or analogous), with cellquest pro software (or analogous) for data analysis. The level of NOCIVA protein present in the samples is determined as the geometric mean fluorescence intensity (MFI) minus the MFI value of the control sample. NOCIVA-depleted cells serve as the negative biological control also in this setup. Positive control is chosen based on prior western blot analysis of AML samples for NOCIVA detection. For research purposes, NOCIVA-specific FACS is also tested and the performance thereof is validated in various solid cancer cell lines and tissue samples (including breast, prostate and HNSCC samples).

REFERENCES

Ciccone, M., Calin, G. A., and Perrotti, D. (2015). From the Biology of PP2A to the PADs for Therapy of Hematologic Malignancies. Frontiers in oncology 5, 21.

Cristóbal I, Blanco F J, Garcia-Orti L, Marcotegui N, Vicente C, Rifon J, Novo F J, Bandres E, Calasanz M J, Bernabeu C, Odero M D (2010). SETBP1 overexpression is a novel leukemogenic mechanism that predicts adverse outcome in elderly patients with acute myeloid leukemia. Blood 115, 615-625.

Junttila, M. R., Puustinen, P., Niemela, M., Ahola, R., Arnold, H., Bottzauw, T., Ala-aho, R., Nielsen, C., Ivaska, J., Taya, Y., et al. (2007). CIP2A inhibits PP2A in human malignancies. Cell 130, 51-62.

Khanna, A., and Pimanda, J. E. (2016). Clinical significance of Cancerous Inhibitor of Protein Phosphatase 2A (CIP2A) in human cancers. Int J Cancer 138, 525-532.

Ventelä, S., Sittig, E., Mannermaa, L., Makela, J. A., Kulmala, J., Loyttyniemi, E., Strauss, L., Carpen, O., Toppari, J., Grenman, R., et al. (2015). CIP2A is an Oct4 target gene involved in head and neck squamous cell cancer oncogenicity and radioresistance. Oncotarget 6, 144-158.

Ventelä, S., Côme, C., Mäkelä, J. A., Hobbs, R. M., Mannermaa, L., Kallajoki, M., Chan, E. K., Pandolfi, P. P., Toppari, J., and Westermarck, J. (2012). CIP2A promotes proliferation of spermatogonial progenitor cells and spermatogenesis in mice. PLoS ONE 7, e33209.

The invention claimed is:

1. A method for detecting the presence of a CIP2A polynucleotide encoding a polypeptide comprising an amino acid sequence having at least 80% sequence identity with SEQ ID NO: 2 outside the region formed by amino acids 546-558 and 100% sequence identity with SEQ ID NO: 2 in the region formed by amino acids 546-558 (SEQ ID NO: 3) in a biological sample, comprising:
   a) contacting polynucleotides prepared from the biological sample with (i) a 3'-primer which specifically hybridizes with a target sequence encompassed by or overlapping with a sequence formed by nucleotides 1636-1674 of SEQ ID NO: 1, wherein said primer has a length of 10-40 nucleotides, and (ii) a 5'-primer which specifically hybridizes with a target sequence encompassed by a sequence formed by nucleotides 1 to 1634 of SEQ ID NO: 1, wherein said primer has a length of 10-40 nucleotides;
   b) performing nucleic acid amplification; and
   c) detecting the amplicon obtained in step b) qualitatively or quantitatively with the oligonucleotide, wherein the oligonucleotide hybridizes with 8-35 consecutive nucleotides of a sequence formed by nucleotides 1636-1674 of SEQ ID NO: 1.

* * * * *

SEQUENCE LISTING

<160> NUMBER OF SEQ ID NOS: 89

<210> SEQ ID NO 1
<211> LENGTH: 2010
<212> TYPE: DNA
<213> ORGANISM: Homo sapiens

<400> SEQUENCE: 1

| | | | | | | |
|---|---|---|---|---|---|---|
| atggactcca | ctgcctgctt | gaagtccttg | ctcctgactg | tcagtcagta | caaagccgtg | 60 |
| aagtcagagg | cgaacgccac | tcagcttttg | cggcacttgg | aggtaatttc | tggacagaaa | 120 |
| ctcacacgac | tatttacatc | aaatcagata | ttaacaagtg | aatgcttgag | ttgccttgta | 180 |
| gagctacttg | aagacccccaa | cataagtgct | tcactgatct | taagtattat | cggtttgctg | 240 |
| tctcaactag | cagtagacat | tgaaaccaga | gattgtcttc | agaatacata | taatctgaat | 300 |
| agtgtgctgg | cgggagtggt | tgtcggagc | agccacactg | attcggtgtt | tttgcagtgc | 360 |
| attcaacttc | tacagaagtt | aacatataat | gtcaaaattt | tctattctgg | tgccaatata | 420 |
| gatgaattaa | ttacgttcct | gatagatcac | attcaatctt | ctgaagatga | gttaaaaatg | 480 |
| ccttgtctag | gattattggc | aaatctttgt | cggcacaatc | tttctgttca | aacgcacata | 540 |
| aagacattga | gtaatgtgaa | atcttttat | cgaactctta | tcaccttgtt | ggcccatagt | 600 |
| agtttaactg | tggttgtgtt | tgcactttca | atattatcca | gtttgacatt | aaatgaagag | 660 |
| gtggggggaaa | agctattcca | tgctcgaaac | attcatcaga | cttttcaact | aatatttaat | 720 |
| attctcataa | acggtgatgg | cactctaact | agaaagtatt | cagttgaccct | actgatggat | 780 |
| ctccttaaga | atcctaaaat | tgctgattat | ctcaccagat | atgagcactt | ttcttcatgt | 840 |
| cttcaccaag | tattaggtct | tcttaatgga | aaggatcctg | attcctcttc | aaaggtttta | 900 |
| gaattacttc | ttgccttctg | ttcagtgact | cagctgcgcc | atatgctcac | tcagatgatg | 960 |
| tttgaacagt | ctccacctgg | cagcgccact | ctgggaagcc | atactaaatg | tttagaacct | 1020 |
| actgtggctc | tactgcgctg | gttaagccaa | cctttggacg | gatcagaaaa | ctgttctgtt | 1080 |
| ttagcattgg | agttgttcaa | ggaaatattt | gaggatgtca | tagatgctgc | taactgttcc | 1140 |
| tcggctgatc | gttttgtgac | ccttctgctg | cctacaatcc | ttgatcaact | tcagttcaca | 1200 |
| gaacaaaatc | tagatgaggc | tttaacaaga | aaaaaatgtg | aaaggattgc | caaggccatt | 1260 |
| gaagttttgt | taactctctg | tggagatgat | acactaaaaa | tgcatattgc | aaaaatcttg | 1320 |
| acaactgtca | gtgtaccac | tcttatagaa | caacaattta | catatggcaa | gattgacctg | 1380 |
| ggatttggaa | caaggttgc | agattctgaa | ttatgcaaac | ttgctgctga | tgtaattttg | 1440 |
| aaaactcttg | atttgattaa | caaacttaaa | ccattggttc | ctggtatgga | agtaagcttc | 1500 |
| tacaaaatac | ttcaggaccc | acgtttgatt | actcctttgg | cttttgcttt | aacgtcagat | 1560 |
| aatagagaac | aagtacagtc | tggactgaga | atattattgg | aggctgctcc | actgccagat | 1620 |
| tttcctgctt | tagtcaacaa | caaaaataca | caggaagctt | ttcaagttac | aagttaaaag | 1680 |
| tggtctgtaa | agctgctcta | ttttgtggtg | gcctgcttgc | ataaactggt | aatctgacat | 1740 |
| gaaacaaaac | cttaagagct | tcaaagggga | atctgcagcc | tcactgaaca | tggaagtctt | 1800 |
| atcctctgcc | tctgtgtgtg | aggccttccc | accattttga | ctgtgtcttg | gcattccctg | 1860 |
| tcttatttgt | gttgtaaata | attttctctt | tgggcattat | ctcagatgtc | cattttatgc | 1920 |
| ttactattta | atgcccttat | ttgacattat | cttgggcgtt | taataaactg | aatgtatatt | 1980 |
| atgaaaaaaa | aaaaaaaaaa | aaaaaaaaaa | | | | 2010 |

```
<210> SEQ ID NO 2
<211> LENGTH: 558
<212> TYPE: PRT
<213> ORGANISM: Homo sapiens

<400> SEQUENCE: 2

Met Asp Ser Thr Ala Cys Leu Lys Ser Leu Leu Thr Val Ser Gln
1               5                   10                  15

Tyr Lys Ala Val Lys Ser Glu Ala Asn Ala Thr Gln Leu Leu Arg His
                20                  25                  30

Leu Glu Val Ile Ser Gly Gln Lys Leu Thr Arg Leu Phe Thr Ser Asn
                35                  40                  45

Gln Ile Leu Thr Ser Glu Cys Leu Ser Cys Leu Val Glu Leu Leu Glu
    50                  55                  60

Asp Pro Asn Ile Ser Ala Ser Leu Ile Leu Ser Ile Ile Gly Leu Leu
65                  70                  75                  80

Ser Gln Leu Ala Val Asp Ile Glu Thr Arg Asp Cys Leu Gln Asn Thr
                85                  90                  95

Tyr Asn Leu Asn Ser Val Leu Ala Gly Val Val Cys Arg Ser Ser His
                100                 105                 110

Thr Asp Ser Val Phe Leu Gln Cys Ile Gln Leu Leu Gln Lys Leu Thr
                115                 120                 125

Tyr Asn Val Lys Ile Phe Tyr Ser Gly Ala Asn Ile Asp Glu Leu Ile
            130                 135                 140

Thr Phe Leu Ile Asp His Ile Gln Ser Ser Glu Asp Glu Leu Lys Met
145                 150                 155                 160

Pro Cys Leu Gly Leu Leu Ala Asn Leu Cys Arg His Asn Leu Ser Val
                165                 170                 175

Gln Thr His Ile Lys Thr Leu Ser Asn Val Lys Ser Phe Tyr Arg Thr
                180                 185                 190

Leu Ile Thr Leu Leu Ala His Ser Ser Leu Thr Val Val Phe Ala
                195                 200                 205

Leu Ser Ile Leu Ser Ser Leu Thr Leu Asn Glu Glu Val Gly Glu Lys
    210                 215                 220

Leu Phe His Ala Arg Asn Ile His Gln Thr Phe Gln Leu Ile Phe Asn
225                 230                 235                 240

Ile Leu Ile Asn Gly Asp Gly Thr Leu Thr Arg Lys Tyr Ser Val Asp
                245                 250                 255

Leu Leu Met Asp Leu Leu Lys Asn Pro Lys Ile Ala Asp Tyr Leu Thr
                260                 265                 270

Arg Tyr Glu His Phe Ser Ser Cys Leu His Gln Val Leu Gly Leu Leu
                275                 280                 285

Asn Gly Lys Asp Pro Asp Ser Ser Lys Val Leu Glu Leu Leu Leu
    290                 295                 300

Ala Phe Cys Ser Val Thr Gln Leu Arg His Met Leu Thr Gln Met Met
305                 310                 315                 320

Phe Glu Gln Ser Pro Gly Ser Ala Thr Leu Gly Ser His Thr Lys
                325                 330                 335

Cys Leu Glu Pro Thr Val Ala Leu Leu Arg Trp Leu Ser Gln Pro Leu
                340                 345                 350

Asp Gly Ser Glu Asn Cys Ser Val Leu Ala Leu Glu Leu Phe Lys Glu
            355                 360                 365

Ile Phe Glu Asp Val Ile Asp Ala Ala Asn Cys Ser Ser Ala Asp Arg
            370                 375                 380
```

```
Phe Val Thr Leu Leu Leu Pro Thr Ile Leu Asp Gln Leu Gln Phe Thr
385                 390                 395                 400

Glu Gln Asn Leu Asp Glu Ala Leu Thr Arg Lys Lys Cys Glu Arg Ile
            405                 410                 415

Ala Lys Ala Ile Glu Val Leu Leu Thr Leu Cys Gly Asp Asp Thr Leu
        420                 425                 430

Lys Met His Ile Ala Lys Ile Leu Thr Thr Val Lys Cys Thr Thr Leu
        435                 440                 445

Ile Glu Gln Gln Phe Thr Tyr Gly Lys Ile Asp Leu Gly Phe Gly Thr
    450                 455                 460

Lys Val Ala Asp Ser Glu Leu Cys Lys Leu Ala Ala Asp Val Ile Leu
465                 470                 475                 480

Lys Thr Leu Asp Leu Ile Asn Lys Leu Lys Pro Leu Val Pro Gly Met
            485                 490                 495

Glu Val Ser Phe Tyr Lys Ile Leu Gln Asp Pro Arg Leu Ile Thr Pro
            500                 505                 510

Leu Ala Phe Ala Leu Thr Ser Asp Asn Arg Glu Gln Val Gln Ser Gly
        515                 520                 525

Leu Arg Ile Leu Leu Glu Ala Ala Pro Leu Pro Asp Phe Pro Ala Leu
530                 535                 540

Val Asn Asn Lys Asn Thr Gln Glu Ala Phe Gln Val Thr Ser
545                 550                 555

<210> SEQ ID NO 3
<211> LENGTH: 13
<212> TYPE: PRT
<213> ORGANISM: Homo sapiens

<400> SEQUENCE: 3

Asn Asn Lys Asn Thr Gln Glu Ala Phe Gln Val Thr Ser
1               5                   10

<210> SEQ ID NO 4
<211> LENGTH: 905
<212> TYPE: PRT
<213> ORGANISM: Homo sapiens

<400> SEQUENCE: 4

Met Asp Ser Thr Ala Cys Leu Lys Ser Leu Leu Leu Thr Val Ser Gln
1               5                   10                  15

Tyr Lys Ala Val Lys Ser Glu Ala Asn Ala Thr Gln Leu Leu Arg His
            20                  25                  30

Leu Glu Val Ile Ser Gly Gln Lys Leu Thr Arg Leu Phe Thr Ser Asn
        35                  40                  45

Gln Ile Leu Thr Ser Glu Cys Leu Ser Cys Leu Val Glu Leu Leu Glu
    50                  55                  60

Asp Pro Asn Ile Ser Ala Ser Leu Ile Leu Ser Ile Gly Leu Leu
65                  70                  75                  80

Ser Gln Leu Ala Val Asp Ile Glu Thr Arg Asp Cys Leu Gln Asn Thr
                85                  90                  95

Tyr Asn Leu Asn Ser Val Leu Ala Gly Val Val Cys Arg Ser Ser His
            100                 105                 110

Thr Asp Ser Val Phe Leu Gln Cys Ile Gln Leu Leu Gln Lys Leu Thr
        115                 120                 125

Tyr Asn Val Lys Ile Phe Tyr Ser Gly Ala Asn Ile Asp Glu Leu Ile
    130                 135                 140
```

```
Thr Phe Leu Ile Asp His Ile Gln Ser Ser Glu Asp Glu Leu Lys Met
145                 150                 155                 160

Pro Cys Leu Gly Leu Leu Ala Asn Leu Cys Arg His Asn Leu Ser Val
            165                 170                 175

Gln Thr His Ile Lys Thr Leu Ser Asn Val Lys Ser Phe Tyr Arg Thr
        180                 185                 190

Leu Ile Thr Leu Leu Ala His Ser Ser Leu Thr Val Val Phe Ala
    195                 200                 205

Leu Ser Ile Leu Ser Ser Leu Thr Leu Asn Glu Val Gly Glu Lys
    210                 215                 220

Leu Phe His Ala Arg Asn Ile His Gln Thr Phe Gln Leu Ile Phe Asn
225                 230                 235                 240

Ile Leu Ile Asn Gly Asp Gly Thr Leu Thr Arg Lys Tyr Ser Val Asp
            245                 250                 255

Leu Leu Met Asp Leu Leu Lys Asn Pro Lys Ile Ala Asp Tyr Leu Thr
            260                 265                 270

Arg Tyr Glu His Phe Ser Ser Cys Leu His Gln Val Leu Gly Leu Leu
        275                 280                 285

Asn Gly Lys Asp Pro Asp Ser Ser Ser Lys Val Leu Glu Leu Leu Leu
290                 295                 300

Ala Phe Cys Ser Val Thr Gln Leu Arg His Met Leu Thr Gln Met Met
305                 310                 315                 320

Phe Glu Gln Ser Pro Pro Gly Ser Ala Thr Leu Gly Ser His Thr Lys
                325                 330                 335

Cys Leu Glu Pro Thr Val Ala Leu Leu Arg Trp Leu Ser Gln Pro Leu
            340                 345                 350

Asp Gly Ser Glu Asn Cys Ser Val Leu Ala Leu Glu Leu Phe Lys Glu
            355                 360                 365

Ile Phe Glu Asp Val Ile Asp Ala Ala Asn Cys Ser Ser Ala Asp Arg
370                 375                 380

Phe Val Thr Leu Leu Pro Thr Ile Leu Asp Gln Leu Gln Phe Thr
385                 390                 395                 400

Glu Gln Asn Leu Asp Glu Ala Leu Thr Arg Lys Lys Cys Glu Arg Ile
            405                 410                 415

Ala Lys Ala Ile Glu Val Leu Leu Thr Leu Cys Gly Asp Asp Thr Leu
            420                 425                 430

Lys Met His Ile Ala Lys Ile Leu Thr Thr Val Lys Cys Thr Thr Leu
            435                 440                 445

Ile Glu Gln Gln Phe Thr Tyr Gly Lys Ile Asp Leu Gly Phe Gly Thr
            450                 455                 460

Lys Val Ala Asp Ser Glu Leu Cys Lys Leu Ala Ala Asp Val Ile Leu
465                 470                 475                 480

Lys Thr Leu Asp Leu Ile Asn Lys Leu Lys Pro Leu Val Pro Gly Met
            485                 490                 495

Glu Val Ser Phe Tyr Lys Ile Leu Gln Asp Pro Arg Leu Ile Thr Pro
            500                 505                 510

Leu Ala Phe Ala Leu Thr Ser Asp Asn Arg Glu Gln Val Gln Ser Gly
            515                 520                 525

Leu Arg Ile Leu Leu Glu Ala Pro Leu Pro Asp Phe Pro Ala Leu
            530                 535                 540

Val Leu Gly Glu Ser Ile Ala Ala Asn Asn Ala Tyr Arg Gln Gln Glu
545                 550                 555                 560

Thr Glu His Ile Pro Arg Lys Met Pro Trp Gln Ser Ser Asn His Ser
```

```
                        565                 570                 575
            Phe Pro Thr Ser Ile Lys Cys Leu Thr Pro His Leu Lys Asp Gly Val
                        580                 585                 590

Pro Gly Leu Asn Ile Glu Glu Leu Ile Glu Lys Leu Gln Ser Gly Met
                        595                 600                 605

Val Val Lys Asp Gln Ile Cys Asp Val Arg Ile Ser Asp Ile Met Asp
                610                 615                 620

Val Tyr Glu Met Lys Leu Ser Thr Leu Ala Ser Lys Glu Ser Arg Leu
            625                 630                 635                 640

Gln Asp Leu Leu Glu Thr Lys Ala Leu Ala Leu Ala Gln Ala Asp Arg
                            645                 650                 655

Leu Ile Ala Gln His Arg Cys Gln Arg Thr Gln Ala Glu Thr Glu Ala
                        660                 665                 670

Arg Thr Leu Ala Ser Met Leu Arg Glu Val Glu Arg Lys Asn Glu Glu
                        675                 680                 685

Leu Ser Val Leu Leu Lys Ala Gln Gln Val Glu Ser Glu Arg Ala Gln
                        690                 695                 700

Ser Asp Ile Glu His Leu Phe Gln His Asn Arg Lys Leu Glu Ser Val
            705                 710                 715                 720

Ala Glu Glu His Glu Ile Leu Thr Lys Ser Tyr Met Glu Leu Leu Gln
                            725                 730                 735

Arg Asn Glu Ser Thr Glu Lys Lys Asn Lys Asp Leu Gln Ile Thr Cys
                        740                 745                 750

Asp Ser Leu Asn Lys Gln Ile Glu Thr Val Lys Lys Leu Asn Glu Ser
                        755                 760                 765

Leu Lys Glu Gln Asn Glu Lys Ser Ile Ala Gln Leu Ile Glu Lys Glu
                770                 775                 780

Glu Gln Arg Lys Glu Val Gln Asn Gln Leu Val Asp Arg Glu His Lys
            785                 790                 795                 800

Leu Ala Asn Leu His Gln Lys Thr Lys Val Gln Glu Glu Lys Ile Lys
                            805                 810                 815

Thr Leu Gln Lys Glu Arg Glu Asp Lys Glu Glu Thr Ile Asp Ile Leu
                        820                 825                 830

Arg Lys Glu Leu Ser Arg Thr Glu Gln Ile Arg Lys Glu Leu Ser Ile
                        835                 840                 845

Lys Ala Ser Ser Leu Glu Val Gln Lys Ala Gln Leu Glu Gly Arg Leu
                        850                 855                 860

Glu Glu Lys Glu Ser Leu Val Lys Leu Gln Gln Glu Glu Leu Asn Lys
            865                 870                 875                 880

His Ser His Met Ile Ala Met Ile His Ser Leu Ser Gly Gly Lys Ile
                            885                 890                 895

Asn Pro Glu Thr Val Asn Leu Ser Ile
                        900                 905

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
ctgagaatat tattggaggc tgctc                                        25

<210> SEQ ID NO 6
```

```
<211> LENGTH: 25
<212> TYPE: DNA
<213> ORGANISM: Artificial Sequence
<220> FEATURE:
<223> OTHER INFORMATION: Primer

<400> SEQUENCE: 6
ctgagaatat tattggaggc tgctc                                    25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
aatagagaac aagtacagtc tggac                                    25

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
tctggactga gaatattatt ggaggc                                   26

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccactgccag attttcctgc                                          20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gctccactgc cagattttcc                                          20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gctgctccac tgccagattt                                          20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
```

-continued cactgccaga ttttcctgct tt                                    22

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
cctgcttgca taaactggta atc                                   23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tggtctgtaa agctgctcta ttt                                   23

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gaatctgcag cctcactgaa                                       20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
agtcttatcc tctgcctctg t                                     21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gtcttggcat tccctgtctt a                                     21

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
gtggcctgct tgcataaac                                        19

<210> SEQ ID NO 19
<211> LENGTH: 19
<212> TYPE: DNA

```
<213> ORGANISM: Artificial Sequence
<220> FEATURE:
<223> OTHER INFORMATION: Primer

<400> SEQUENCE: 19
ctgctccact gccagattt                                                    19

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cagcctcact gaacatggaa                                                   20

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
aaaagtggtc tgtaaagctg ctc                                               23

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
tgccagattt tcctgcttta g                                                 21

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
cagtctggac tgagaatatt attgga                                            26

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
cagtctggac tgagaatatt attgga                                            26

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tggcttttgc tttaacgtca g                                                 21
```

<210> SEQ ID NO 26
<211> LENGTH: 35
<212> TYPE: DNA
<213> ORGANISM: Artificial Sequence
<220> FEATURE:
<223> OTHER INFORMATION: Probe

<400> SEQUENCE: 26
cctgctttag tcaacaacaa aaatacacag gaagc         35

<210> SEQ ID NO 27
<211> LENGTH: 35
<212> TYPE: DNA
<213> ORGANISM: Artificial Sequence
<220> FEATURE:
<223> OTHER INFORMATION: Probe

<400> SEQUENCE: 27
cctgctttag tcaacaacaa aaatacacag gaagc         35

<210> SEQ ID NO 28
<211> LENGTH: 35
<212> TYPE: DNA
<213> ORGANISM: Artificial Sequence
<220> FEATURE:
<223> OTHER INFORMATION: Probe

<400> SEQUENCE: 28
cctgctttag tcaacaacaa aaatacacag gaagc         35

<210> SEQ ID NO 29
<211> LENGTH: 22
<212> TYPE: DNA
<213> ORGANISM: Artificial Sequence
<220> FEATURE:
<223> OTHER INFORMATION: Probe

<400> SEQUENCE: 29
tgtgtgtgag gccttcccac ca         22

<210> SEQ ID NO 30
<211> LENGTH: 22
<212> TYPE: DNA
<213> ORGANISM: Artificial Sequence
<220> FEATURE:
<223> OTHER INFORMATION: Probe

<400> SEQUENCE: 30
tgtgtgtgag gccttcccac ca         22

<210> SEQ ID NO 31
<211> LENGTH: 22
<212> TYPE: DNA
<213> ORGANISM: Artificial Sequence
<220> FEATURE:
<223> OTHER INFORMATION: Probe

<400> SEQUENCE: 31
tgtgtgtgag gccttcccac ca         22

<210> SEQ ID NO 32
<211> LENGTH: 22
<212> TYPE: DNA
<213> ORGANISM: Artificial Sequence
<220> FEATURE:

```
<223> OTHER INFORMATION: Probe

<400> SEQUENCE: 32
tgtgtgtgag gccttcccac ca                                          22

<210> SEQ ID NO 33
<211> LENGTH: 22
<212> TYPE: DNA
<213> ORGANISM: Artificial Sequence
<220> FEATURE:
<223> OTHER INFORMATION: Probe

<400> SEQUENCE: 33
tgtgtgtgag gccttcccac ca                                          22

<210> SEQ ID NO 34
<211> LENGTH: 24
<212> TYPE: DNA
<213> ORGANISM: Artificial Sequence
<220> FEATURE:
<223> OTHER INFORMATION: Probe

<400> SEQUENCE: 34
tgcagcctca ctgaacatgg aagt                                        24

<210> SEQ ID NO 35
<211> LENGTH: 24
<212> TYPE: DNA
<213> ORGANISM: Artificial Sequence
<220> FEATURE:
<223> OTHER INFORMATION: Probe

<400> SEQUENCE: 35
cagtttatgc aagcaggcca ccac                                        24

<210> SEQ ID NO 36
<211> LENGTH: 27
<212> TYPE: DNA
<213> ORGANISM: Artificial Sequence
<220> FEATURE:
<223> OTHER INFORMATION: Probe

<400> SEQUENCE: 36
agtcttatcc tctgcctctg tgtgtga                                     27

<210> SEQ ID NO 37
<211> LENGTH: 24
<212> TYPE: DNA
<213> ORGANISM: Artificial Sequence
<220> FEATURE:
<223> OTHER INFORMATION: Probe

<400> SEQUENCE: 37
tgactgtgtc ttggcattcc ctgt                                        24

<210> SEQ ID NO 38
<211> LENGTH: 28
<212> TYPE: DNA
<213> ORGANISM: Artificial Sequence
<220> FEATURE:
<223> OTHER INFORMATION: Probe

<400> SEQUENCE: 38
tctctttggg cattatctca gatgtcca                                    28
```

```
<210> SEQ ID NO 39
<211> LENGTH: 8
<212> TYPE: DNA
<213> ORGANISM: Artificial Sequence
<220> FEATURE:
<223> OTHER INFORMATION: Probe

<400> SEQUENCE: 39 ctgcctct                                                                    8

<210> SEQ ID NO 40
<211> LENGTH: 8
<212> TYPE: DNA
<213> ORGANISM: Artificial Sequence
<220> FEATURE:
<223> OTHER INFORMATION: Probe

<400> SEQUENCE: 40 tggtggcc                                                                    8

<210> SEQ ID NO 41
<211> LENGTH: 8
<212> TYPE: DNA
<213> ORGANISM: Artificial Sequence
<220> FEATURE:
<223> OTHER INFORMATION: Probe

<400> SEQUENCE: 41 tggtggcc                                                                    8

<210> SEQ ID NO 42
<211> LENGTH: 8
<212> TYPE: DNA
<213> ORGANISM: Artificial Sequence
<220> FEATURE:
<223> OTHER INFORMATION: Probe

<400> SEQUENCE: 42 tccactgc                                                                    8

<210> SEQ ID NO 43
<211> LENGTH: 8
<212> TYPE: DNA
<213> ORGANISM: Artificial Sequence
<220> FEATURE:
<223> OTHER INFORMATION: Probe

<400> SEQUENCE: 43 tccactgc                                                                    8

<210> SEQ ID NO 44
<211> LENGTH: 8
<212> TYPE: DNA
<213> ORGANISM: Artificial Sequence
<220> FEATURE:
<223> OTHER INFORMATION: Probe

<400> SEQUENCE: 44 ggaggctg                                                                    8

<210> SEQ ID NO 45
<211> LENGTH: 20
<212> TYPE: DNA
<213> ORGANISM: Artificial Sequence
<220> FEATURE:
<223> OTHER INFORMATION: Primer
```

<400> SEQUENCE: 45
ttatgcaagc aggccaccac    20

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
gtttctgttt cctgttgtct ataggc    26

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
aatagagcag ctttacagac cac    23

<210> SEQ ID NO 48
<211> LENGTH: 27
<212> TYPE: DNA
<213> ORGANISM: Artificial Sequence
<220> FEATURE:
<223> OTHER INFORMATION: Primer

<400> SEQUENCE: 48
atatacattc agtttattaa acgccca    27

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
tggacatctg agataatgcc ca    22

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
ggacatctga gataatgccc aaag    24

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
acatctgaga taatgcccaa agaga    25

<210> SEQ ID NO 52
<211> LENGTH: 25

```
<212> TYPE: DNA
<213> ORGANISM: Artificial Sequence
<220> FEATURE:
<223> OTHER INFORMATION: Primer

<400> SEQUENCE: 52
cgcccaagat aatgtcaaat aaggg                                              25

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
cacacagagg cagaggataa g                                                  21

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
gcagaggata agacttccat gtt                                                23

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
aataagacag ggaatgccaa ga                                                 22

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
acatctgaga taatgcccaa aga                                                23

<210> SEQ ID NO 57
<211> LENGTH: 24
<212> TYPE: DNA
<213> ORGANISM: Artificial Sequence
<220> FEATURE:
<223> OTHER INFORMATION: Primer

<400> SEQUENCE: 57
cgcccaagat aatgtcaaat aagg                                               24

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
```
gcagaggata agacttccat gt                                            22

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
gagcagcttt acagaccact t                                             21

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
cagtcaaaat ggtgggaagg                                               20

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
ttcatgtcag attaccagtt tatgc                                         25

<210> SEQ ID NO 62
<211> LENGTH: 25
<212> TYPE: DNA
<213> ORGANISM: Artificial Sequence
<220> FEATURE:
<223> OTHER INFORMATION: Primer

<400> SEQUENCE: 62
catgtcagat taccagttta tgcaa                                         25

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
tgtaacttga aaagcttcct gtgta                                         25

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
aaaagcttcc tgtgtatttt tgttg                                         25

<210> SEQ ID NO 65
<211> LENGTH: 24
<212> TYPE: DNA
<213> ORGANISM: Artificial Sequence

```
<220> FEATURE:
<223> OTHER INFORMATION: Primer

<400> SEQUENCE: 65
tgaaaagctt cctgtgtatt tttg                                              24

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66
ggcattgttt gctgctatac ttt                                               23

<210> SEQ ID NO 67
<211> LENGTH: 27
<212> TYPE: DNA
<213> ORGANISM: Artificial Sequence
<220> FEATURE:
<223> OTHER INFORMATION: Primer

<400> SEQUENCE: 67
gaacagataa gaaaagagtt gagcatt                                           27

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
cgaccttcta attgtgcctt tt                                                22

<210> SEQ ID NO 69
<211> LENGTH: 8
<212> TYPE: DNA
<213> ORGANISM: Artificial Sequence
<220> FEATURE:
<223> OTHER INFORMATION: Probe

<400> SEQUENCE: 69 cttcctcc                                                                8

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
tcacccacac rgtgcccatc tacgc                                             25

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
cagcggaacc gctcattgcc aatgg                                             25
```

<210> SEQ ID NO 72
<211> LENGTH: 26
<212> TYPE: DNA
<213> ORGANISM: Artificial Sequence
<220> FEATURE:
<223> OTHER INFORMATION: Probe

<400> SEQUENCE: 72
atgccctccc ccatgccatc ctgcgt                                   26

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
acccactcct ccacctttga                                          20

<210> SEQ ID NO 74
<211> LENGTH: 22
<212> TYPE: DNA
<213> ORGANISM: Artificial Sequence
<220> FEATURE:
<223> OTHER INFORMATION: Primer

<400> SEQUENCE: 74
ttgctgtagc caaattcgtt gt                                       22

<210> SEQ ID NO 75
<211> LENGTH: 30
<212> TYPE: DNA
<213> ORGANISM: Artificial Sequence
<220> FEATURE:
<223> OTHER INFORMATION: Probe

<400> SEQUENCE: 75
acgaccactt tgtcaagctc atttcctggt                               30

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
agtgccctgg agatgagttg                                          20

<210> SEQ ID NO 77
<211> LENGTH: 22
<212> TYPE: DNA
<213> ORGANISM: Artificial Sequence
<220> FEATURE:
<223> OTHER INFORMATION: Primer

<400> SEQUENCE: 77
tttgaggcta tctgtgaagt gc                                       22

<210> SEQ ID NO 78
<211> LENGTH: 22
<212> TYPE: DNA
<213> ORGANISM: Artificial Sequence
<220> FEATURE:
<223> OTHER INFORMATION: Probe -continued

```
<400> SEQUENCE: 78 cccccagtgag gtataaagag ga                                           22

<210> SEQ ID NO 79
<211> LENGTH: 18
<212> TYPE: DNA
<213> ORGANISM: Artificial Sequence
<220> FEATURE:
<223> OTHER INFORMATION: Primer

<400> SEQUENCE: 79
gggcgtgtga ccgtagct                                                 18

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
cgctattcgc aatcagggtt a                                             21

<210> SEQ ID NO 81
<211> LENGTH: 21
<212> TYPE: DNA
<213> ORGANISM: Artificial Sequence
<220> FEATURE:
<223> OTHER INFORMATION: Probe

<400> SEQUENCE: 81
agcacggtca ccttcgacgg g                                             21

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
acaggtttgc agaacccatc                                               20

<210> SEQ ID NO 83
<211> LENGTH: 21
<212> TYPE: DNA
<213> ORGANISM: Artificial Sequence
<220> FEATURE:
<223> OTHER INFORMATION: Primer

<400> SEQUENCE: 83
ggacagcagg tcactaacag c                                             21

<210> SEQ ID NO 84
<211> LENGTH: 8
<212> TYPE: DNA
<213> ORGANISM: Artificial Sequence
<220> FEATURE:
<223> OTHER INFORMATION: Probe

<400> SEQUENCE: 84 tccagtgt                                                             8

<210> SEQ ID NO 85
```

```
<211> LENGTH: 21
<212> TYPE: DNA
<213> ORGANISM: Artificial Sequence
<220> FEATURE:
<223> OTHER INFORMATION: Primer

<400> SEQUENCE: 85
cagagggagc actatgtctg c                                                   21

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
gcttttaatt ttgcttcttc tgct                                                24

<210> SEQ ID NO 87
<211> LENGTH: 19
<212> TYPE: DNA
<213> ORGANISM: Artificial Sequence
<220> FEATURE:
<223> OTHER INFORMATION: Primer

<400> SEQUENCE: 87
catgatgatc cacggcttc                                                      19

<210> SEQ ID NO 88
<211> LENGTH: 22
<212> TYPE: DNA
<213> ORGANISM: Artificial Sequence
<220> FEATURE:
<223> OTHER INFORMATION: Primer

<400> SEQUENCE: 88
tcagggagag atggcatatg ta                                                  22

<210> SEQ ID NO 89
<211> LENGTH: 2730
<212> TYPE: DNA
<213> ORGANISM: Homo sapiens

<400> SEQUENCE: 89
atttatttag gacccacgtt tgattactcc tttggctttt gctttaacgt cagataatag         60
agaacaagta cagtctggac tgagaatatt attggaggct gctccactgc cagattttcc        120
tgctttagtg tgagttgtaa tcatttgcag tgtatctctt gtggtgttgg aatacccctgc       180 tatgtctctt tagtcctcag tatagataca caagcaaatt agtgaattga agacttcatt        240
gtaatagtaa ttttcaagt gatttctaaa aatgtttgat tcttataaat gaaaagttca         300
gatgtatact cactcaggga aaagctagat ccaggcagtt aaatgttctt caggtactat        360
ccctctatgt ctctagccac ttcttttttaa tgataacttc tggacactct taagcctaca      420
tcctcccagt ttagttcctc catagaaaga gctttttcctt cctgactgtt taaggaaaag      480
gtctaagcat tagtcattga ccaggcctgg gttatccatg agaacgatgt ggactaaaag       540
ttagttggga taggagaata ggagagttcc taaagaaaaa aatctgaact tttatcagaa       600
agtggaaaaa tgacaaccag gcaaaatttt ctactatact cgttactttc aagcaataag      660
aatatttgca attatgtttg aaaaaaaatt cagatttcag ggctctctga actaaatgtc       720
tattaggagt ctggtttaaa attttttttaa gtcatttata tgtatgaatt tgtaaaaatg      780
```

```
gtttgaataa tttgaagtag ttgataaaca ggtaagatat tccctgtata ccgggatcag    840
caaactggcc agtggacagg catctgtttt tgtaaatagt tttattggaa tatggccaca    900
cccactcatt tttatactct gtctatgttg ctttcactct ataaaagcag aattgagtaa    960
ttgtgacaga gaccagatag gtccttgagt ctaaaatact tactatcttg acctataaga   1020
aaaagtgctg gtccatgcta tatgctattc actgatttag cgattccact tttcagaatt   1080
agcaatttag gtcatcatac cttaagagtt aaagtatggg atgtaagacc tagagaacat   1140
ataaccaaaa ttcccttaat tttataataa atattttttt aacagcaaca acaaaaatac   1200
acaggaagct tttcaagtta caagttaaaa gtggtctgta aagctgctct attttgtgat   1260
ggcctgcttg cataaactgg taatctgaca tgaaacaaaa ccttaagagc ttcaaagggg   1320
aatctgcagc ctcactgaac atggaagtct tatcctctgc ctctgtgtgt gaggccttcc   1380
caccattttg actgtgtctt ggcattccct gtcttatttg tgttgtaaat aattttctct   1440
ttgggcatta tctcagatgt ccattttatg cttactattt aatgccctta tttgacatta   1500
tcttgggcgt ttaataaact gaatgtatat tatggatgca ttggtaggta gggttttgt    1560 gtgtgtgtat ttacttgttt gttttcgaga cagggtctca ctctatcacc cagactgggg   1620
tgcagtggtg tgatcatgac tcactgcagc ttcgacctct ggggctcaag tgatattccc   1680
aactcaaccc cctgagtagc ggggaccaca ggcttgtgcc accacaactg cttaattaat   1740
ttattttttt atagaggggt ctcaccaggt tgcccaggct tgtctcgaac tcttggactc   1800
aagtgatcct cccaaagtgc tgcggttaca ggtgtgagcc accatgccca gcctataata   1860
aattaggctg agtgcctgcc atcttgcagt ttgcacttta gttaagagat aagtgaaaaa   1920 aatatttttgt tttgtggtag aaagcgtgtt ccagataaag gaacagctca tatgaaggcc   1980
tgaggtagga gaaagagagg atttaaagg gttagaatgg aagtcaggtt ggtgaaaagt    2040
atgtactgag tgagaaagga aaaggactaa ggacgtaaag gccaggtgat atcacccatg   2100
ataagaacat tattctgacc agtaccaata actttgtact tattacagat aatccacact   2160
cataaactag tcttacaatg cctccaaacc agaggtgaag ctgtcattat aaaaggttag   2220
aaacagaaaa gtgggtgctc tggaaaattc agaatatttc ccaagacttc atttcatcat   2280
ggtctccaag attatttgaa gacttctatt caaaaaaagg acccattctt aaaaattccc   2340
taattctgca ctaagtctgc cttttcttct attttcgtat aattttttttt ccttctttt   2400 gactcccatt cagacttgga gaaagtatag cagcaaacaa tgcctataga caacaggaaa   2460
cagaacatat acccagaaaa atgccctggc aatcatcaaa tcacagtttt ccaacatcaa   2520
taaagtgttt aactcctcat ttgaaagatg gtgttcctgg attgaatatt gaagaattaa   2580
tagagaaact tcagtctgga atggtggtga gtgaaaaaat agcaattata acctggtaca   2640
tattagctat atgtcagtcc caattataac gtgtatctaa acactgtcag gtacagattt   2700
cactattgaa acccttaatat aagaaataac                                   2730
```